(12) United States Patent
Grobshtein et al.

(10) Patent No.: US 9,297,913 B2
(45) Date of Patent: Mar. 29, 2016

(54) IMAGING SYSTEM AND METHOD OVERCOMING OBSTRUCTIONS USING INDEPENDENTLY CONTROLLABLE DETECTORS

(71) Applicant: General Electric Company, Schenectady, NY (US)

(72) Inventors: Yariv Grobshtein, Haifa (IL); Jean-Paul Bouhnik, Zichron Yaacov (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/721,407

(22) Filed: May 26, 2015

(65) Prior Publication Data

US 2015/0276949 A1 Oct. 1, 2015

Related U.S. Application Data

(63) Continuation-in-part of application No. 14/612,398, filed on Feb. 3, 2015, which is a continuation of application No. 14/135,751, filed on Dec. 20, 2013, now Pat. No. 9,029,791.

(51) Int. Cl.
| | |
|---|---|
| *G01T 1/164* | (2006.01) |
| *G01T 1/29* | (2006.01) |
| *G01T 1/161* | (2006.01) |
| *A61B 6/03* | (2006.01) |
| *A61B 6/00* | (2006.01) |
| *G06T 11/00* | (2006.01) |

(52) U.S. Cl.
CPC ............... *G01T 1/2985* (2013.01); *A61B 6/037* (2013.01); *A61B 6/4258* (2013.01); *A61B 6/4266* (2013.01); *G01T 1/161* (2013.01); *G01T 1/1642* (2013.01); *G06T 11/005* (2013.01); *A61B 6/503* (2013.01); *A61B 6/545* (2013.01); *A61B 6/547* (2013.01)

(58) Field of Classification Search
CPC ...... A61B 6/037; A61B 6/469; G01T 1/2985; G01T 1/249
See application file for complete search history.

(56) References Cited

U.S. PATENT DOCUMENTS

| | | | |
|---|---|---|---|
| 5,675,513 | A | 10/1997 | Hammer |
| 5,949,842 | A | 9/1999 | Schafer et al. |
| 6,256,404 | B1 | 7/2001 | Gordon et al. |

(Continued)

FOREIGN PATENT DOCUMENTS

| | | |
|---|---|---|
| EP | 2275989 | 1/2011 |
| WO | 2014165472 A1 | 10/2014 |

*Primary Examiner* — Kiho Kim
(74) *Attorney, Agent, or Firm* — Lucas Divine

(57) ABSTRACT

Imaging systems, methods, and computer readable mediums are provided. Image detectors are installed in a gantry to detect image information related to a subject. If obstructions are detected related to the field of view of an image detector, a system matrix can be updated accordingly. Thus, upon image reconstruction, artifacts related to obstructions can be minimized or altogether eliminated. This system can be a Nuclear Medicine (NM) imaging system to acquire Single Photon Emission Computed Tomography (SPECT) image information.

20 Claims, 23 Drawing Sheets

(56) References Cited

U.S. PATENT DOCUMENTS

| | | |
|---|---|---|
| 6,636,214 B1 | 10/2003 | Leather et al. |
| 7,223,240 B2 | 5/2007 | Murashita |
| 7,555,164 B2 | 6/2009 | Lin |
| 7,601,966 B2 * | 10/2009 | Ben-Haim ............ G01T 1/1648 250/394 |
| 7,829,856 B2 | 11/2010 | Jansen et al. |
| 8,194,237 B2 | 6/2012 | Cronin et al. |
| 8,421,021 B2 | 4/2013 | Sachs et al. |
| 8,748,827 B2 * | 6/2014 | Zilberstein ............ G01T 1/1611 250/363.04 |
| 2015/0065873 A1 | 3/2015 | Tsukerman et al. |

* cited by examiner

IMAGING SYSTEM AND METHOD OVERCOMING OBSTRUCTIONS USING INDEPENDENTLY CONTROLLABLE DETECTORS

PRIORITY AND REFERENCE TO RELATED APPLICATIONS

This application is a continuation-in-part of U.S. patent application Ser. No. 14/612,398, entitled "IMAGING SYSTEM USING INDEPENDENTLY CONTROLLABLE DETECTORS", filed Feb. 3, 2015, which is a continuation of U.S. patent application Ser. No. 14/135,751, entitled "IMAGING SYSTEM USING INDEPENDENTLY CONTROLLABLE DETECTORS", filed Dec. 20, 2013 and patented on May 12, 2015 as U.S. Pat. No. 9,029,791, the disclosures of which is incorporated by reference herein as if set forth in their entirety.

BACKGROUND

The subject matter disclosed herein relates generally to medical imaging systems, and more particularly to Nuclear Medicine (NM) imaging systems which can be Single Photon Emission Computed Tomography (SPECT) imaging systems.

In NM imaging, such as SPECT imaging, radiopharmaceuticals are administered internally to a patient. Detectors (e.g., gamma cameras), typically installed on a gantry, capture the radiation emitted by the radiopharmaceuticals and this information is used to form images. The NM images primarily show physiological function of, for example, the patient or a portion of the patient being imaged.

While such systems have proven extremely useful at providing quality images with diagnostic value, further refinement is possible. Conventional SPECT imaging systems have limitations in design and/or operational characteristics. For example, in some instances additional hardware configurations are needed to increase the system flexibility and reduce costs.

In such a NM system with multiple detectors, obstructions may block the field of view of one or more detectors. Such obstructions may be caused by other detectors in the system. Systems and methods are needed to provide enhanced image quality while dealing with obstruction issues.

BRIEF DESCRIPTION

In accordance with an embodiment, an imaging system is provided that includes a gantry; a plurality of imaging detector units, each detector unit comprising a detector arm installed in the gantry and a detector head; wherein at least one of the detector heads is movable such that its angle can be altered with respect to its detector arm; a controller in communication with the plurality of detector units, configured to control the angle of the at least one detector head; and wherein if the controller detects an obstruction in a field of view a detector head, the controller updates a system matrix to include obstruction information related to the obstruction. Further, the controller may receive image information detected by the detector units; reconstruct the image information into images using the updated system matrix; and output the images to a display, printer, memory, or computer network. The system matrix may be a data structure in memory that describes the physics of the imaging system. Further, the updating of the system matrix to include obstruction information includes inputting zeros into the matrix elements related to the pixels that are obstructed.

In addition, the controller may perform the steps of adjusting the angle of a detector head; acquiring location and orientation information for the detector head at its new angle; generating a field of view determination for the detector head based on said location and orientation information; determining whether a region-of-interest (ROI) of a imaging subject is within the detector field of view; if the ROI is within the field of view, the controller acquires image information detected by the detector head even if an obstruction is within the field of view; and if the ROI is outside the field of view, the controller does not acquire image information detected by the detector head. The controller may acquire the location and orientation information from a position sensor installed in the detector unit.

The detector head movement may be a pivot movement with respect to its respective detector arm. Each detector head is extendable and retractable with respect to the gantry along its respective detector arm. Each detector head may include a plurality of detector elements that detect SPECT emissions.

In accordance with an embodiment, an imaging method and a non-transitory computer readable storage medium having stored thereon a computer program comprising instructions which may be executed by a computer may be provided that perform steps of pivoting a detector head of an image detector unit, the image detector unit attached to a gantry; determining whether an obstruction is in the field of view of the detector head; and updating a system matrix to include information related to the obstruction. Steps may be included for receiving image information detected by the detector unit; reconstructing the image information into images using the updated system matrix; and outputting the images to a display, printer, memory, or computer network. Image information may include SPECT information. Further, the detector head may comprise a plurality of detector elements and a collimator; the field of view is determined by the coverage of said detector elements and a collimator configuration.

Further, steps may be included for acquiring location and orientation information for the detector head at its current angle; generating a current field of view determination for the detector head based on said location and orientation information; determining whether a region-of-interest (ROI) of a imaging subject is within the detector current field of view; if the ROI is within the current field of view, a controller acquires image information detected by the detector head even if an obstruction is within the field of view; and if the ROI is outside the current field of view, the controller does not acquire image information detected by the detector head. The system may also perform steps of determining whether a ROI is within a field of view of the detector head; second pivoting of the detector head in the same direction as the first pivoting if the ROI is within the field of view; and stopping the pivoting of the detector head if a detector pixel in the field of view reaches an end of the ROI before reaching an obstruction.

The system matrix may be updated based on installation information and subject scan information. Further, updating of the system matrix may include information related to the obstruction by inputting zeros into the matrix elements related to the pixels that are obstructed. The system matrix may be a data structure in memory that describes the physics of the imaging system.

DETAILED DESCRIPTION

Figure 1:
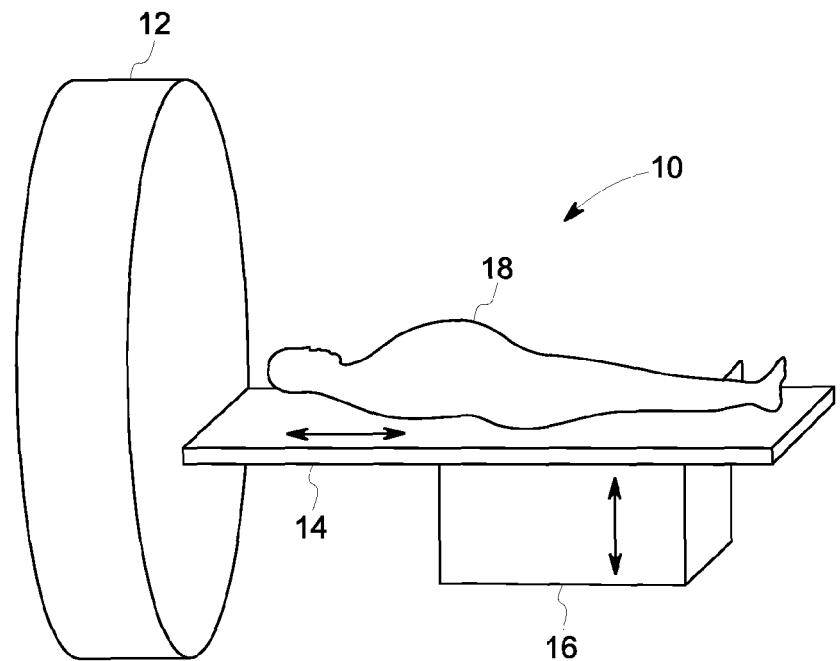
FIG. 1 is a perspective view of an exemplary medical imaging system, in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with a plurality of different types of imaging detectors mounted thereto. For example, in various embodiments of an NM imaging system, a Single Photon Emission Computed Tomography (SPECT) imaging scanner is provided that includes a plurality of detectors with a combination of different types of detectors that acquire SPECT image information. The various embodiments may include detectors formed from different materials, having different configurations or arrangements, having different collimation, etc. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects other than people.

A medical imaging system 10 may be provided as illustrated in FIG. 1. A subject 18 can be a human patient in one embodiment. It should be noted that the subject 18 does not have to be human. It can be some other living creature or inanimate object in various embodiments. The subject 18 can be placed on a pallet 14 that can move a subject horizontally for locating the subject in the most advantageous imaging position. The bed mechanism 16 can raise and lower the pallet 14 vertically for locating the subject in the most advantageous imaging position. The gantry 12 is shown as circular in one embodiment. In other embodiments the gantry 12 may be of any shape such as square, oval, "C" shape, or hexagonal.

Figure 2:
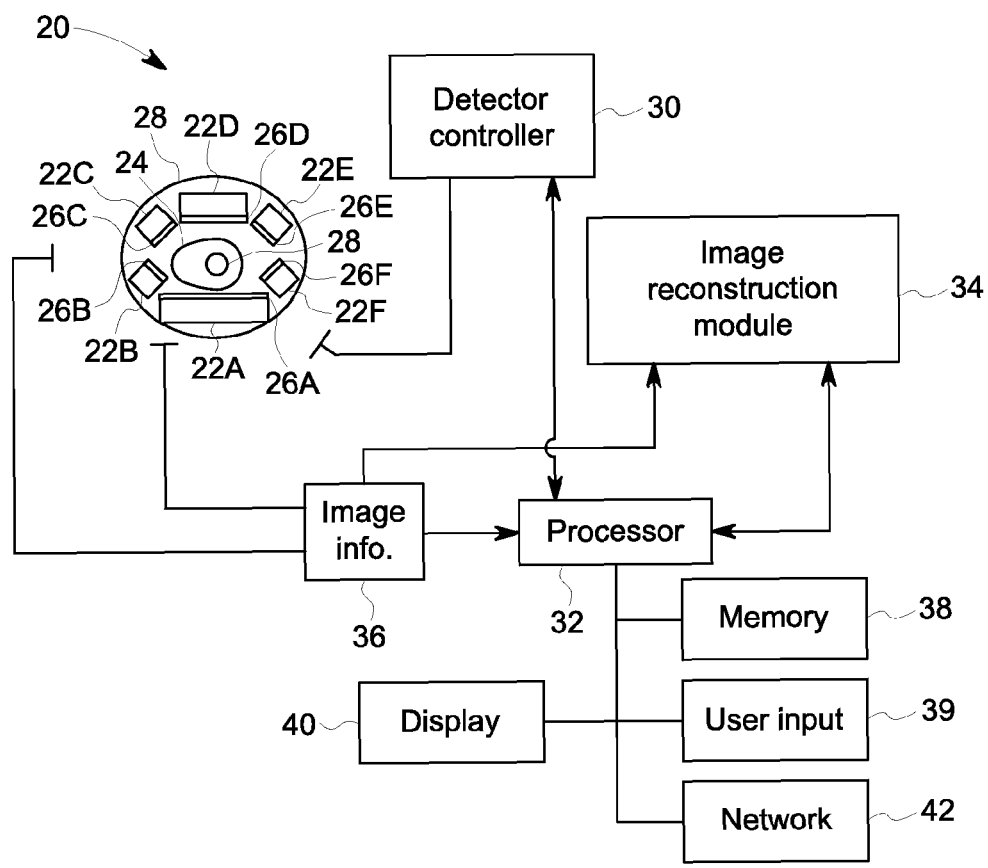
FIG. 2 is a simplified schematic block diagram illustrating a medical imaging system, in accordance with an embodiment.

FIG. 2 shows the medical imaging system 20 in accordance with another embodiment. The medical imaging system 20 may be provided having a plurality of NM cameras configured as SPECT detector columns 22a-22f. It should be noted that the various embodiments are not limited to the medical imaging system 20 having six detector columns 22 as shown or to the sizes or shapes of the illustrated detector columns 22. For example, the medical imaging system 20 may include more or less detector columns 22 having different shapes and/or sizes, or formed from different materials. The medical imaging system 20 in various embodiments is configured as a hybrid SPECT system having a plurality of detector columns 22, wherein at least two of the detectors are formed from different materials, have different configurations or arrangements, have different collimation, or are otherwise different. Detector columns can be called detector units in some embodiments.

In operation, a subject, such as a patient 24, is positioned in proximity to the one or more of the detector columns 22 for imaging. The imaging system 20 can then re-adjust the detector columns 22 further from or closer to the patient 24 or patient area of interest as needed, which is heart 28 in an example embodiment. Imaging of the patient 24 is performed by one or more of the detector columns 22. The imaging by each of the detector columns 22 may be performed simultaneously, concurrently, or sequentially.

The position of the detector columns 22 may be varied, including the relative position between detector columns 22, tilt, angle, swivel, etc. of the detector columns 22. Additionally, each of the detector columns 22 may have a corresponding collimator 26a-26f mounted or coupled thereto. The collimators 26a-26f likewise may be of different types. One or more detector columns 22 may be coupled to a different type of collimator 26 (e.g., parallel hole, pin-hole, fan-beam, cone-beam, etc.). Accordingly, in various embodiments, the detector column 22 wholly includes collimator 26.

The detector columns 22 may include single crystal, or multi-crystal, detectors or pixelated detectors or scintillator based detectors that are configured to acquire SPECT image data. For example, the detector columns 22 may have detector elements formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum(III) bromide ($LaBr_3$), among others. Additionally suitable components may be provided. For example, the detector columns 22 may be coupled to photosensors, such as an array of Photo-Multiplier Tubes (PMTs), an Avalanche Photodiode Detector (AFD), etc.

The imaging system 20 can also include a detector controller 30 that operates to control the movement of the detector columns 22 and/or the collimators 26. For example, the detector controller 30 may control movement of the detector columns 22, such as to rotate or orbit the detector columns 22 around a patient 24, and which may also include moving the detectors closer or farther from the patient 24 and pivoting/swiveling the detector columns 22, such that more localized movements or motions are provided. The detector controller 30 additionally may control the orbital rotation of the detector columns 22 around the edges of the gantry bore, such that the detector columns 22 are at a new angle to the patient 24 than previously. The detector controller 30 may also optionally control movement of the collimators 26, such as independently of the detector columns 22. It should be noted that one or more the detector columns 22 and/or the collimators 26 may move during imaging operation, move prior to, but remain stationary during imaging operation, or may remain in a fixed positioned or orientation. In various embodiments, the detector controller 30 may be a single unit controlling movement of both the detector columns 22 and the collimators 26, may be separate units, or may be a single unit controlling only operation of the detector columns 22 or may be a single unit controlling only operation of the collimators 26.

The imaging system 20 also includes an image reconstruction module 34 configured to generate images from acquired image information 36 received from the detector columns 22. For example, the image reconstruction module 34 may operate using NM image reconstruction techniques to generate SPECT images of the patient 24, which may include an object of interest, such as the heart 28 of the patient. The image reconstruction techniques may be determined based on the installation status of detector column 22 acquiring the image information 36 and sending to image reconstruction module 34 and/or processor 32.

Variations and modifications to the various embodiments are contemplated. For example, in a multi-headed system, namely a system having two or more detector columns 22, each detector column 22 may be formed from different materials and have different collimators 26. Accordingly, in at least one embodiment, one detector combination may be configured to obtain information for an entire field of view (FOV), such as the entire spine, while another detector combination is configured to focus on a smaller region of interest (ROI) to provide higher quality information (e.g., more accurate photon counting). Additionally, information acquired by one detector combination may be used to adjust the position, orientation, etc. of at least one other detector combination during imaging.

The image reconstruction module 34 may be implemented in connection with or on a detector controller 30 and/or processor 32 that is coupled to the imaging system 20. Optionally, the image reconstruction module 34 may be implemented as a module or device that is coupled to or installed in the detector controller 30 and/or processor 32. Each processing module may be a separate hardware module or software module, or combined together into one chip or module in various embodiments.

The image information 36 received by the processor 32 and/or image reconstruction module 34 may be stored for a short term (e.g., during processing) or for a long term (e.g., for later offline retrieval) in a memory 38. The memory 38 may be any type of data storage device, which may also store databases of information. The memory 38 may be separate from or form part of the processor 32. A user input 39, which may include a user interface selection device, such as a computer mouse, trackball and/or keyboard is also provided to receive a user input. The user input may direct the processor 32 to send a detector control signal to the detector controller 30 for alteration of the detector column 22 arrangement in the gantry bore. Optionally, the user input 39 may be considered by the processor 32 as a suggestion and the processor 32 may choose to not execute the suggestion based on criteria.

Thus, during operation, the output from the detector columns 22, which may include the image information 36, such as projection data from a plurality of detector/gantry angles is transmitted to the processor 32 and the image reconstruction module 34 for reconstruction and formation of one or more images. The reconstructed images and other user output can be transmitted to a display 40 such as a computer monitor or printer output. The reconstructed images and other user output can also be transmitted to a remote computing device via network 42.

Different combinations and variations of detector columns 22 and/or collimators 26 will now be described. It should be noted that the various embodiments are not limited to a particular detector, collimator, or detector combination, but may include any imaging system having a plurality of different types of detector columns 22 and/or collimators 26, for example, having at least two detector columns 22 of a different type or design. Additionally, the number of detector columns 22 and the arrangement thereof may be varied as desired or needed, for example, based on the type of imaging to be performed or the type of image information to be acquired. Accordingly, various embodiments include the imaging system 20 having a plurality of detector columns 22, wherein at least two of the detector columns 22 are different and are configured to perform imaging of the patient 24 (or other object).

For example, in one embodiment, illustrated in FIG. 2, a configuration is provided having one detector column 22a formed from one material and the remaining detector columns 22b-22l formed from a different material. In the illustrated embodiment, the detector column 22a is formed from a NaI material and the remaining detector columns 22b-22l are formed from a CZT material. Accordingly, in this configuration, a single NaI detector column 22a and a plurality of CZT detector columns 22b-22l are provided. The detector columns 22a-22l may be sized and shaped the same or differently. For example, in the embodiment illustrated in FIG. 2, the NaI detector column 22a is larger than each of the CZT detector columns 22b-22l, such that the NaI detector column 22a can image the entire patient 24 and the CZT detector columns 22b-22l are configured to focus on a portion of the patient 24, such as the heart 28. In this embodiment, one or more of the CZT detector columns 22b-22l may be positioned and oriented at different angles or tilted differently to provide focused imaging. However, one or more of the CZT detector columns 22b-22l may be angled or tilted the same. In the embodiment of FIG. 2, the CZT detector columns 22b-22l are angled such that together the CZT detector columns 22b-22l focus on the overall body of the patient 24, instead of on a particular ROI, such as the heart 28. Thus, one or more detector columns 22 may be arranged and configured to cover an entire FOV of an imaged, while one or more other detectors are arranged and configured to cover a focused FOV within the object.

It should be noted that as used herein, a set of detectors is generally referred to as the detector columns 22 and a set of collimators is generally referred to as the collimators 26. Moreover, the use of letter designations after the numeral designation for the detector columns 22 and collimators 26 are used for ease of illustration and do not necessarily represent the same detector columns 22 or collimators 26 in the various embodiments or figures. Thus, the letter designation represents the relative positioning of the detector columns 22 or collimators 26 and not necessarily the type or kind of detector. Additionally, the size and shape of the detector columns 22 may be varied as desired or needed.

In FIG. 2, the collimators 26a-26l may be the same or may be different. For example, the collimator 26a may be of a first type, such as a parallel hole collimator, while the collimators 26b-26l may have different types (e.g., converging, diverging or pinhole) based on a desired or required sensitivity or resolution, as well as the position and orientation of the detector column 22 on which the collimator 26 is coupled. Thus, the collimators 26 may be of any type.

It should be noted that motion of one or more imaging detector columns may be in directions other than strictly axially or radially, and optionally, motions in several motion directions may be used. Moreover, the motions of the imaging detector columns are coordinated in various embodiments as described herein. Therefore, the term detector controller may be used to indicate a collective name for all motion controllers. It should be noted that the various controllers may be combined, for example, as shown in FIG. 3

Figure 3:
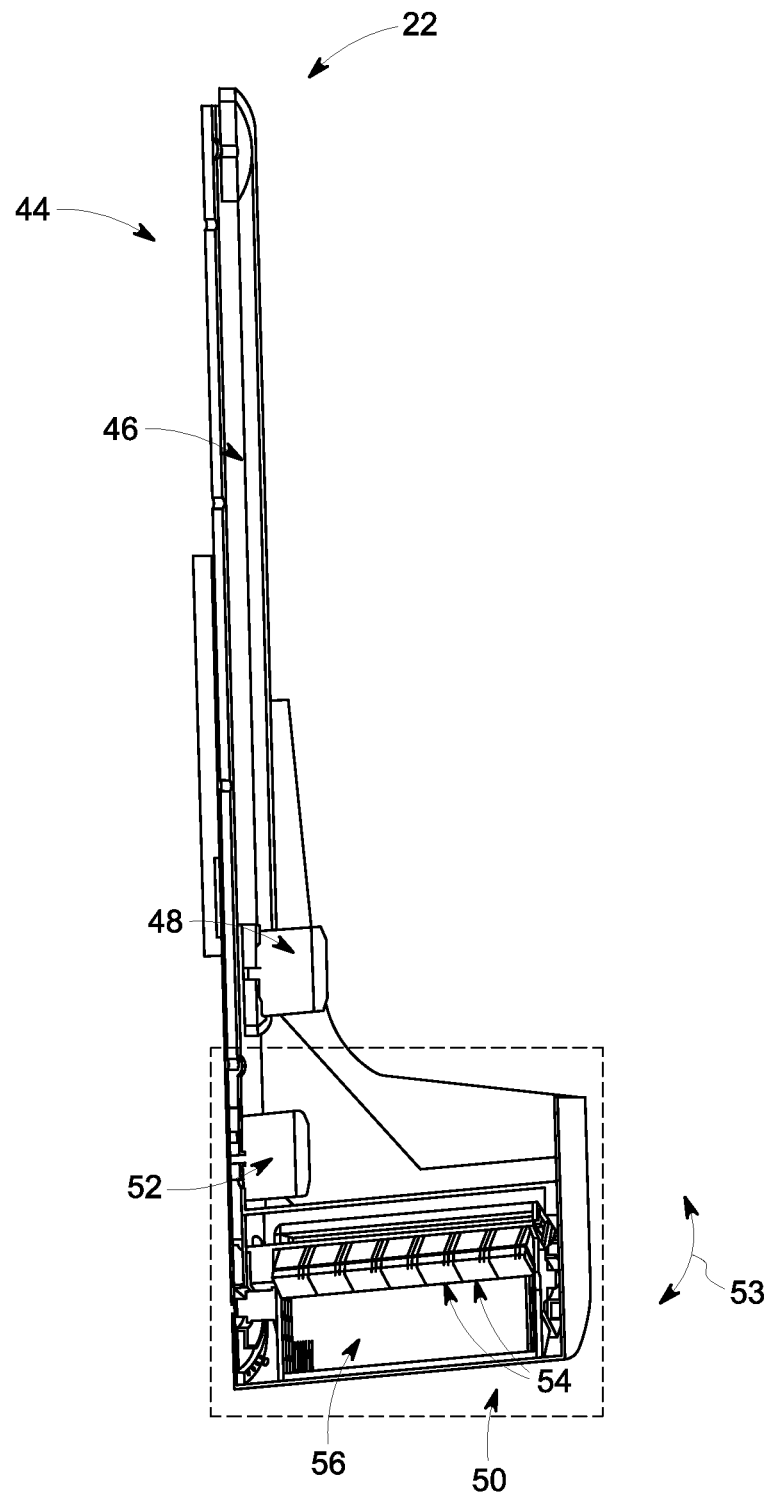
FIG. 3 is a detailed view of a detector column design, in accordance with an embodiment.

FIG. 3 shows a more detailed implementation of detector column 22 in accordance with an embodiment. Column arm 44 attaches to a gantry and provides support for and includes a radial motion rail 46, radial motion motor 48, and detector head 50. The radial motion motor 48 controls the movement of the detector head 50 by extending or retracting the detector head 50 along the radial motion rail 46. This provides customizability and flexibility to the imaging system. The detector column can include telescopic covers that allow it to extend and contract as it moves radially in and out.

Detector head 50 includes a sweep motor 52, detector elements 54, and collimator 56. The detector elements 54 can be CZT modules or other detector element modules discussed throughout for detecting imaging data. Sweep motor 52 controls the rotation angle of the detector head 50 in relation to the arm 44. The sweep pivoting axis 53 shows the rotation angle axis of the detector head 50. The detector controller 30 can provide instruction and control to either or both of the radial motion motor 48 and sweep motor 52. Thus, each detector column 22 is independently controllable in the radial location as well as the angle of tilt of the detector head 50. The radial motion motor 48 and sweep motor 52 can be two separate motors as shown in the embodiment of FIG. 3. Alternatively, the functionality of the two motors may be provided by one motor.

Figure 4A:
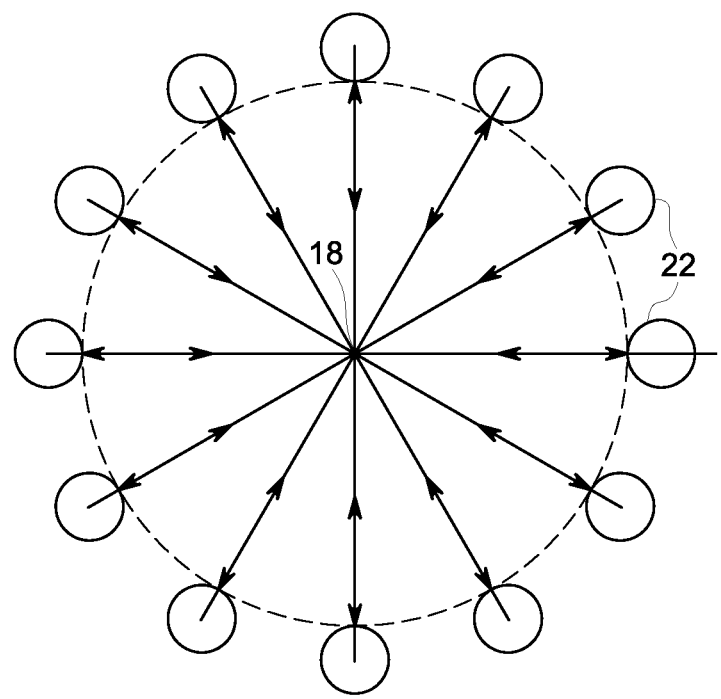
FIG. 4A is a diagram illustrating a radial construction and approach to image detection, in accordance with an embodiment.

FIG. 4A shows a radial construction of an imaging system where twelve detector columns 22 are placed at a consistent angle, thirty degrees in this example, from each other along the inside of a gantry bore. Thus, the detector columns 22 are uniformly distributed in this example. Each detector column 22 is movable along a radial axis. This allows the detector columns 22 to be closer or further from a subject 18 for imaging. The circles in the figure depict the location of the detector head 50 of detector column 22. The detector columns are shown along the dotted line as their outer limit position in this view of one embodiment. The dual head radial arrows depict the in-out direction of motion of the detector columns 22.

In an embodiment, a detector column may attach to the gantry, either the stationary portion or a rotary member attached thereto, by a pivot end. In conjunction with a pivot motor, the system may pivot the detector column at different angles to the gantry. This may be performed with a separate pivot motor, or as actuated by another motor or actuator in the system. Thus, the detector column may have at least three controllable motions: a pivot function for the whole arm, extending and retracting the detector head, and sweeping the detector head in various directions.

Figure 4B:
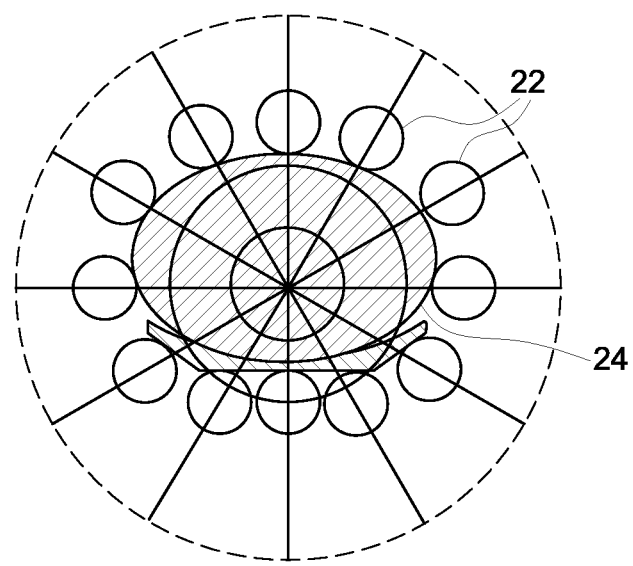
FIG. 4B is a diagram of the detector columns controlled to move at different points of their radial axis to best scan the specific shape of a subject, in accordance with an embodiment.

FIG. 4B shows a radial construction where twelve detector columns 22 have their heads placed at a consistent angle and have been moved radially inward to be in positions close to a patient 24. As FIG. 4B shows, some of the detector heads are further towards the center of their radial axis than others. This allows for high-quality imaging results with varied-sized objects.

Figure 5:
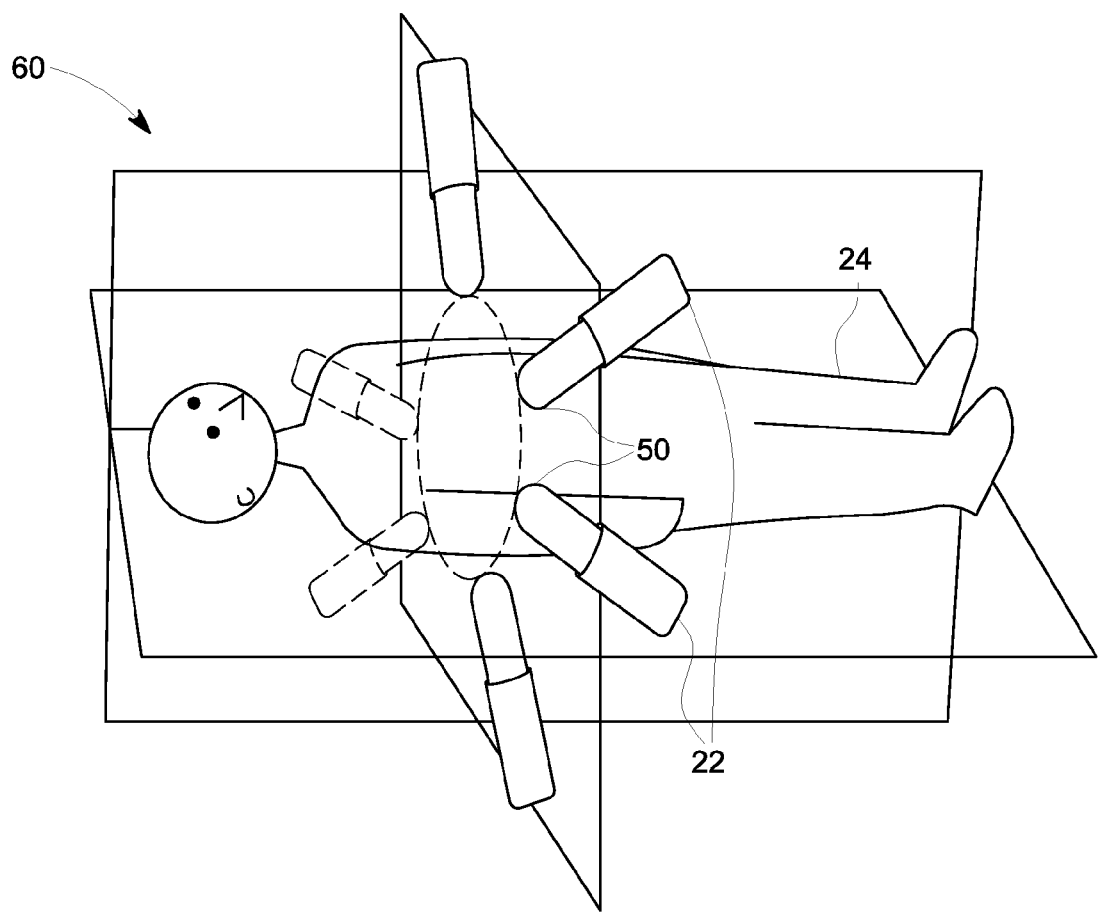
FIG. 5 is a patient centric view of an exemplary medical imaging system, in accordance with an embodiment.

FIG. 5 shows a NM medical imaging system 60 scanning the mid-section of a patient 24 where the detector columns 22 including detector heads 50 are only partially populated, according to one embodiment. Compared to a fully populated system, such as FIG. 4A and FIG. 4B, a partially populated system includes the installation of a partial amount of detector columns 22 that an imaging system is configured to support. FIG. 5 also demonstrates the planes of scanning including the sagittal plane, coronal plane, and transverse plane. Based on the specific ROI or type of image scan selected, imaging of a patient may only need to be focused in areas of these planes. Some embodiments herein are directed towards tailoring partially populated imaging systems, such as NM imaging system 60 for maximal image quality and lowest scan time given the situation and installation information constraints.

Figure 6:
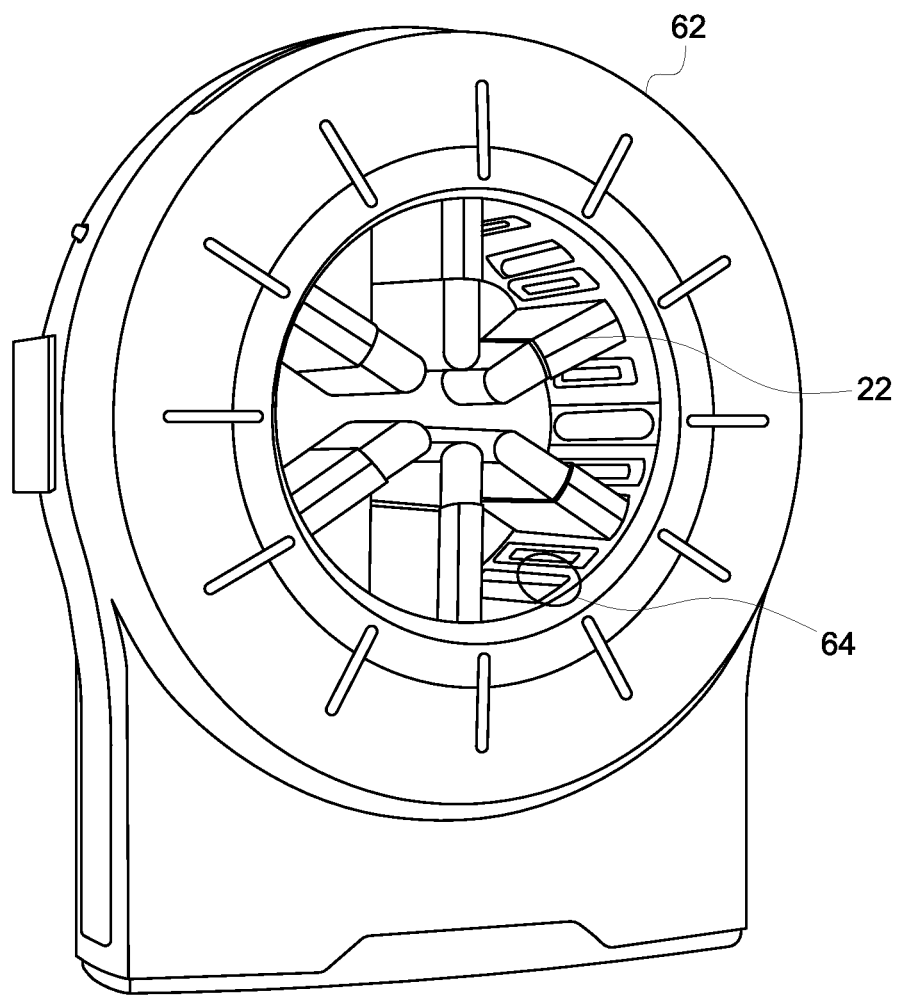
FIG. 6 is a perspective view of a gantry design with detector columns placed in a partially populated configuration, in accordance with an embodiment.

FIG. 6 shows a gantry 62 that can support twelve detector columns 22. The gantry 62 can contain all of the features of the FIG. 2 system in one embodiment. Only six detector columns 22 have been installed in gantry 62. This could be for lower cost of the system, easier maintenance, or other reasons, for example. Thus, the system of FIG. 6 is a partially populated NM imaging system. It is partially populated because the installation information for the system indicates that the system can support twelve detector columns 22, but only six detector columns 22 are installed. The locations where a detector column can be installed or attached can be called receiver locations 64 in some embodiments. The detector columns 22 in FIG. 6 are shown in a radially extended position. The detector columns 22 of this embodiment can be detached by a non-technical operator. They can be detached from one of the twelve receiver locations 64 and snapped, screwed, clamped, or otherwise attached, to one of the open receiver locations 64 around the gantry 62. Thus, detector columns 22 are detachable and attachable to create further system configurations. This system, in some embodiments, can be considered a modular system. A non-technical operator can be one who has not had specialized or advanced training on the installation and adjustment of the imaging system. A technical operator could be a field engineer, for example.

Installation information can be dynamically updated by processor 32 or detector controller 30 based on information from installation verification elements in receiver locations 64, and stored in memory 38 in one embodiment. Installation verification elements can be any sort of switch, button, sensor, or other device that detects the presence of hardware installed or not installed in the system. Installation verification elements of receiver locations 64 are one way that the system can detect and update installation information. Installation information in one embodiment relates to the detector column arm 44 being physically attached to gantry 62. Further, installation information in another embodiment detects both physical attachment plus a fully functioning arm. In this embodiment, if any of the radial motion motor 48, sweep motor 52, and/or detector elements 54 are inoperable, even though the detector column 22 is attached to the gantry 62, the installation information could indicate the detector column as uninstalled and/or inoperable. Installation information can also indicate the population of specific detector elements 54, as further discussed below.

Installation information is also called configuration information in some embodiments. This is because installation information gives information related to the current hardware configuration in the imaging system, and can be dynamically updated. Thus, installation information, sometimes called configuration information, is not just the initial setup information of the system when delivered to a customer, but is information dynamically updated based on many hardware factors throughout the lifetime of the system.

Figure 7A:
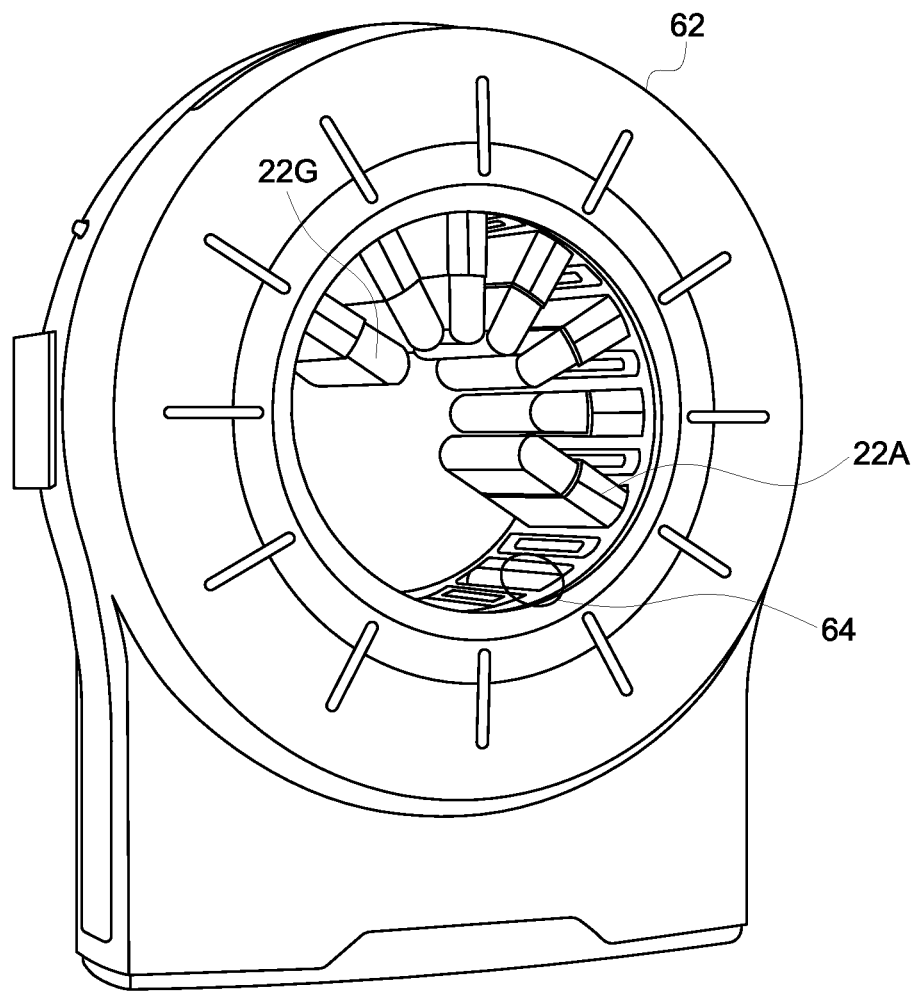
FIG. 7A is a perspective view of a gantry design with detector columns aligned for a supine positioned subject, in accordance with an embodiment.

FIG. 7A shows a gantry 62 that can support the installation and operation of twelve detector columns 22. Only seven detector columns 22 have been installed in gantry 62. This is an example of a partially populated imaging system. The detector columns 22 in FIG. 7A are shown in a radially extended manner, but not as radially extended as shown in FIG. 6. This configuration may be best for a supine patient where the heart, as an example of a ROI, is near the top and side of the gantry. The detector controller 30 can identify from the installation information that there are seven installed detector columns 22 and in which receiver locations 64 they reside around the bore of gantry 62. Then the detector controller 30 rotates the detector columns 22 around the bore to the ideal position for the particular region of interested based on user input 39 or information of the test and patient from other sources, such as memory 38 or network 42. This ideal position can also be called the position location essential for imaging information. Thus, moving the detector columns 22 and detector heads 50 into the best position for capturing essential imaging information for each type of procedure is important and is done by the embodiments.

Figure 7B:
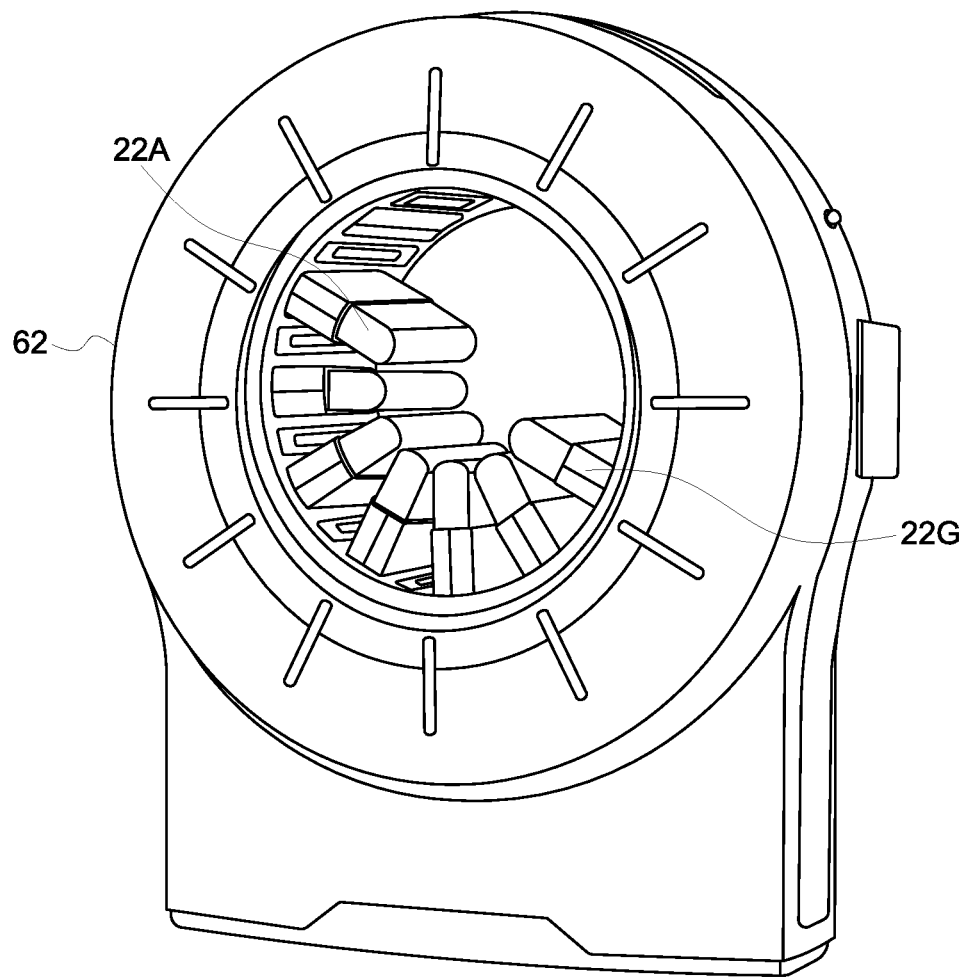
FIG. 7B is a perspective view of a gantry design with detector columns aligned for a prone positioned subject, in accordance with an embodiment.

FIG. 7B shows a gantry 62 where the seven detector columns 22 have been rotated by machinery in an orbital manner inside the gantry 62 that is controlled by the detector controller 30 to move the detector columns 22 into positions with new radial axes to a patient. This may be completed through a rotary member attached to the stationary gantry in one embodiment. The detector columns can be rotated rotate three-hundred sixty degrees around a subject to be imaged, which is patient 24 in this example. As can be seen from comparing FIG. 7A to FIG. 7B, detector column 22a has been rotated from an axial position below patient 24 to an axial position above patient 24. Detector column 22g, consequently, has moved from above to below the patient in this example. The example in FIG. 7B may be best for prone patients where the heart, as an example of a ROI, is near the bottom and side of the gantry.

Figure 8:
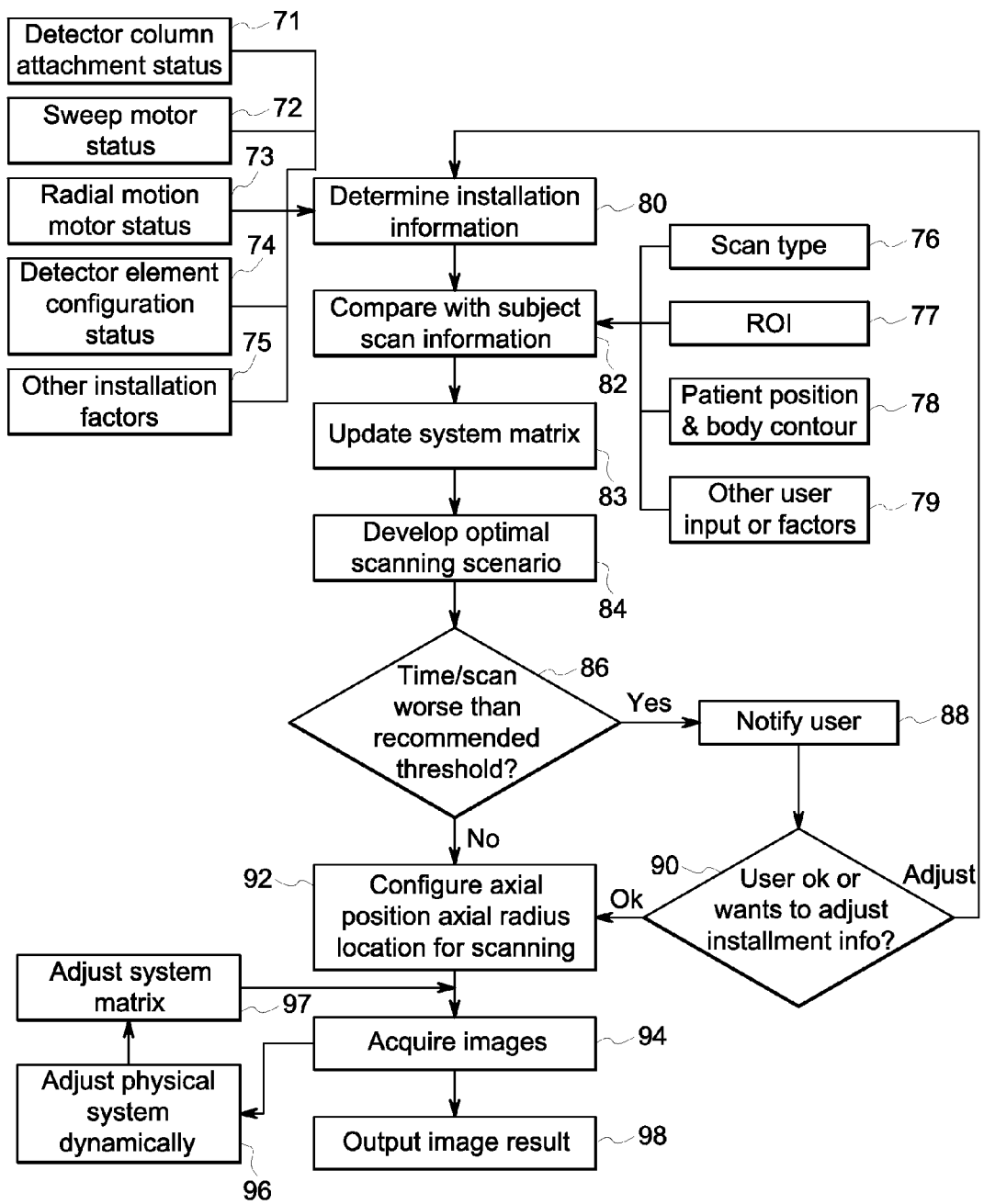
FIG. 8 is a flowchart of a method for usage of the medical imaging system, in accordance with an embodiment.

FIG. 8 is a flowchart depicting a method of operation with respect to one embodiment. The steps as shown do not necessarily have to flow in the order as listed, but are shown in this order just as an example.

In step 80, the system determines installation information. This helps determine what operations and features are available in the system. Installation information, in some embodiments, can included detector column attachment status 71 which indicates in which receiver locations 64 detector columns 22 are installed and in which receiver locations 64 detector columns 22 are not installed. This can tell the system both how far each detector unit can be extended radially as well as how much orbital movement of the detector units will need to occur during operation. Installation information can further include sweep motor status 72. This status can indicate whether each detector column 22 has a sweep motor 52 for head rotation capability, whether the sweep motor 52 is operable, and its range of motion (in circumstances when some detector heads 50 are configured to rotate further than others), or not responding. Installation information can further include radial motion motor status 73. This status can indicate whether each detector column 22 has a radial motion motor 48, its radial motion distance, radial location status, and whether or not the motor is currently operable. Installation information can further include detector element configuration status 74. This status can indicate the specific locations where detector elements 54 are installed and specific locations where detector elements 54 could be installed but are not installed. See FIGS. 16-17 for example. This status can also indicate what materials are being used to detect the imaging data. Each detector column or detector element could have different scintillator or semi-conductor materials installed. This detector element configuration status 74 can also indicate what collimator 56 structure is used in the detector head. As mentioned above, different collimators 56 can be utilized in different detector heads 50. Installation information can further include other installation factors 75, including gantry rotation ability. This is an indication of how many degrees of rotation (or how many 'steps') the gantry can rotate detector columns around the orbit of the gantry. Installation information can further include other installation factors 75 such as the room the imaging system is set up in, factors input by a user, safety information, and other types of information about the installation of the system overall, not just the installation status of the components in the imaging system. For example, many SPECT systems are placed in SPECT/CT (computed tomography) combined system, and the system may also acquire information related to what CT setup is installed.

In step 82, the system compares the installation information with what a specific imaging scan will be and subject information. The imaging scan type information 76 (such as CT, SPECT, PET, MRI, or can be related to the specific radiopharmaceutical being used or the type of medical examination performed) can be considered. The region of interest information 77 (such as cardiac, brain, thyroid) can be considered. The patient position information 78 on the pallet or bed can be considered. In addition, the system may be enabled to determine body contour information in step 78. The subject size, age, gender, weight, and other medical characteristics (patient body-type information, or patient medical information or subject specific information) can impact the process relating to other user input factors 79. The imaging scan is generally a NM imaging scan based on acquiring SPECT data, but the system could be used in other scanning arrangements for other types of imaging information.

In step 83, the system can update, or adjust, a system matrix. It should be noted that when reference is made herein to a system matrix, this generally refers to a matrix that describes the probability that activity in a particular voxel in the image space is recorded by a particular pixel in the detector space. The system matrix is essentially a mathematical description of the physics of the system (e.g., physics of collimators of an imaging system, angles, FOV, installation information, attenuation, geometrical calibration, etc.) at various times and positions of the system. The system matrix includes the possible hardware configurations of the different angles. This includes the installation information related to detector columns and detector elements. In one embodiment, the system matrix may be provided as a table (e.g., a correlation table) or other data structure that describes the relationship at specified times between what signal or value would be observed at a detector element based on the activity or intensity (e.g., emitted radiation) at a given voxel of the imaging volume. That is, the system matrix describes the relationship between activity within the imaging volume and expected observations at the detector for a given geometry and at a given time. The system may include a separate system matrix processor that determines a system matrix for use when reconstructing an image, or utilize processor 32. The system matrix may be stored in a memory of a nuclear medicine imaging system. System matrix based image reconstruction accordingly can be performed using a system matrix determined in accordance with various embodiments.

In an alternate embodiment, step 83 may be performed after step 84. In such systems, it may be best to know the exact scanning scenario planned in order to update the system matrix. This can be because the positions and angles of the detector head views may be included in the scanning scenario. This information may be useful to be update into the system matrix before a scan begins. In an alternate embodiment, step 83 may be performed both before and after step 84.

The system may run an initial system matrix determination in step 80 detailing the setup and operation of the system in matrix form for image reconstruction. Then, the system matrix may be successively updated as step 83 and step 97 are performed.

In step 84, the imaging system 20 develops an optimal scanning scenario based on the installation information, subject scan information, and system matrix. For example, if the scan is a cardiac scan and the subject patient is small, a selected scenario would set the radial extension of the arms to high and the arms will be recommended to move orbitally towards the sides of the gantry closest to the heart. If the angle of the subject is difficult, the scenario may include rotating some of the detector heads 50 to be more accurately aligned towards the subject. The optimal scanning scenario may include method 400, below.

In step 86, the system makes a decision whether the scanning scenario can be performed within a threshold time. This can also be called a total imaging operation time prediction. This determination considers how long it will take the system to do the full requested imaging based on the imaging time plus system rearrangement time when it is being reconfigured to get additional scanning data. The threshold can be based on an 'acceptable' time set by a user, a subject patient preferred time, a normalized time compared to most scans of the type being done, and/or related to a threshold of safety. The total imaging operation time prediction also considers how long it may take to adjust the patient and how long it takes to adjust the detector columns, detector heads, and/or detector elements. If the time to complete the optimal scanning scenario is higher than a threshold, the system goes to step 88, otherwise continuing on to step 86.

In step 88, a user is notified that the current installation setup of the system may not be able to complete the requested scan in a threshold time. A list of options may also be presented to the user relating to steps the user can take to mitigate any issues or override the issue.

In step 90, the user decides whether to alter the installation arrangement/setting of the system or not. The user can input a response back to the system of their intention. The user can adjust the system manually, in some respects, and automatically through computer control in other respect. If a user adjusts the system, thus altering installation information, the method returns to step 80 to re-evaluate the installation information. If the user is OK with the time threshold being met or exceeded, the system can proceed to step 92.

In step 92, the system performs the physical modifications recommended in the optimal scanning scenario. This can include configuring the detector column axial position around the gantry orbit, the axial radius location for scanning (how far or close to patient along the axial radius), detector head angle as controlled by the sweep motor, and other physical adjustments discussed throughout.

In step 94, the subject is in the system and the images are acquired. If multiple physical positions of the detector columns 22, detector heads 50, and/or detector elements 54 are needed, the system adjusts them during the imaging operation at step 96. This is an example of dynamically adjusting of the physical system.

In step 97, the system can update, or adjust, the system matrix. This may include the method 400 below. Effectively, in this manner, the updated system matrix is modified or updated to represent the various geometries, obstructions, and relative camera positions present in the data acquisition step and the corresponding observed projection data is essentially binned based on time and camera geometry.

In step 98, the final requested image data is output. A reconstruction algorithm may be applied after the image data acquisition or proactively during the image data acquisition. The output can be to a display, network connected computing device, a printer, picture archive and communication system (PACS) or other output location.

Because the imaging system of at least one embodiment can start with limited installation equipment, the system can perform lower-cost imaging, while also providing upgradability. For example, if a hospital has a small budget and only will perform cardiac scans, they can purchase a system with detector columns setup best for cardiac and not including additional detector columns that can add additional cost. The hospital can still do other types of scans, but will have to wait longer for the system to re-adjust to different image scan scenarios to handle the different scan type. This can add time and sometimes provide a lower quality image than a fully populated or otherwise customized system. The hospital can upgrade and purchase more detector columns, or detector columns with the optional detector head sweep feature, or detector columns with the optional detector radius extension feature, or detector columns with multiple types of image acquisition materials and install them into the system for improved performance. This also applies to detector elements. Detector elements are a driver of cost as well. So a hospital, for example, could purchase one with lower detector element count (with longer scan time, seen for example in FIG. 16B) and upgrade later.

Figure 9:
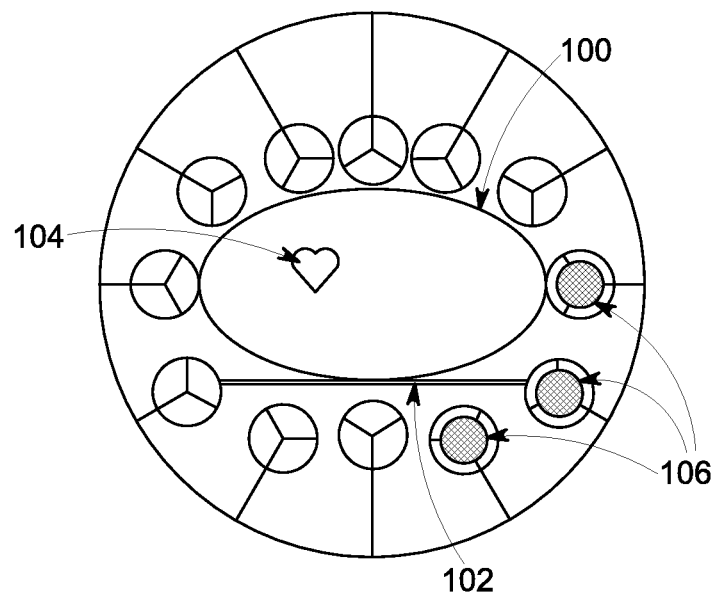
FIG. 9 is a radial construction view of a gantry design with detector columns aligned for a cardiac application, in accordance with an embodiment.

FIG. 9 shows the front view of an imaging system specifically set to target a cardiac image. A patient 100 lies on a bed 102, which could also be similar to the pallet 14 and bed mechanism 16 of FIG. 1, with their heart 104 on the left side of the system in this view. For this cardiac application, distant locations 106 can either be un-populated (empty) of any detector columns or they can be set to inactive to not receive images (such as, to save electricity). In this case, the unused detector columns may be retracted and not advance towards the patient. This can also be beneficial when one of the detector columns in the system has a broken aspect, such as one of its motors, wires, arm, or detector elements. They system can orbitally move that broken detector column into a distant location 106 to not be used in the current scan. A notification can be sent to the user or operator regarding the issue, the user or operator can be at a local display or remote facility. The system, in this embodiment, does not need to use any detector columns in distant locations 106 because they are too far from the subject, for example, and the distance reduces resolution of the image and adds attenuation from the gamma ray source, patient heart 104 in this example. Thus, the image contribution of any detector columns in distant locations 106 is negligible.

Figure 10:
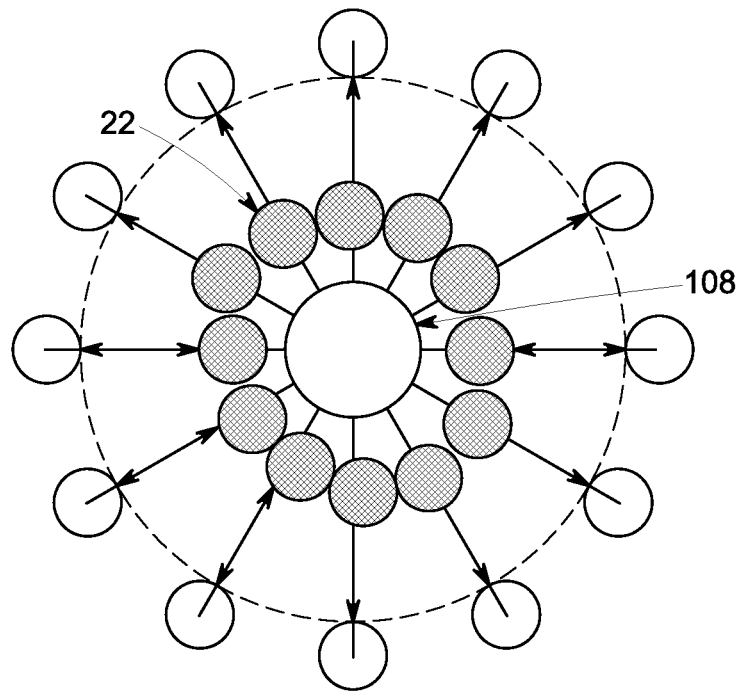
FIG. 10 is a radial construction view of a gantry design with detector columns aligned for a brain or pediatric application, in accordance with an embodiment.

FIG. 10 shows the front view of an imaging system specifically set to target a small subject such as a brain, a limb, or pediatric image. In this imaging operation, the patient area 108 is smaller than a full body. The detector columns 22 have their heads extend radially from their starting position on the outer limits of the gantry towards the patient 108 to get the best image resolution by being closer, in this example. This example shows a case where a fully populated, all twelve detector column receiver locations in the gantry are filled with detector columns, system is not necessarily ideal, because the arms collide as they try to get the closest distance from the patient area 108.

Figure 11:
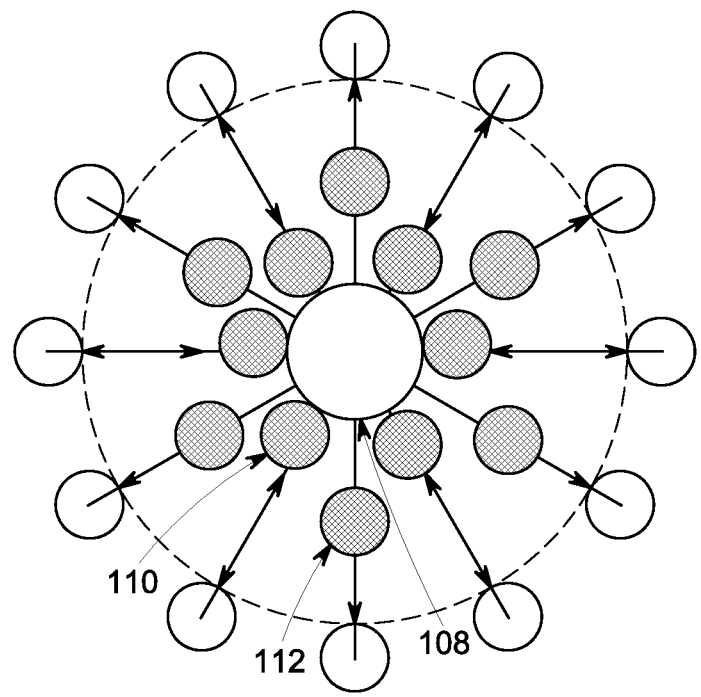
FIG. 11 is radial construction view of a gantry design with detector columns aligned differentially for a brain or pediatric application, in accordance with an embodiment.

FIG. 11 shows another front view of an imaging system specifically set to target a brain or pediatric image. This is a similar situation to FIG. 10, but the system, following the flowchart steps of FIG. 8 or FIG. 13, determines the installation information (in this case, as an example, a fully populated system with twelve detector columns where the radial motion motors are all in operation), takes in the subject scan information (either the fact that the scan type is a head—small in size, or the subject type is a child—small in size), and develops an optimal scanning scenario. This case includes some fully extended detector columns 110, in this case every other, with some not-fully extended detector columns 112. In FIG. 10, an implementation with fully extended detector columns 110 was not possible because of detector column collision. By not uniformly extending the detector columns, such an implementation is possible in the scenario of FIG. 11.

Figure 12:
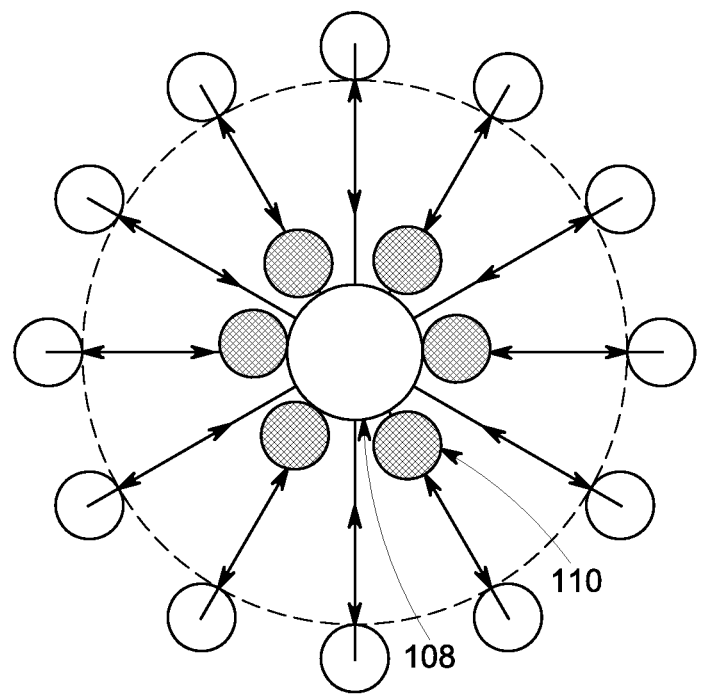
FIG. 12 is radial construction view of a gantry design with partially populated detector columns for a brain or pediatric application, in accordance with an embodiment.

FIG. 12 shows another front view of an imaging system specifically set to target a brain or pediatric image. In this system, similar to FIG. 6, only half of the possible receiver locations for detector column installation have detector columns installed. A user, either technically savvy or not technically savvy depending on specific hardware implementation, could have removed the detector columns that were not needed from the system. A customer could order from the supplier an imaging system with only some of the detector columns installed, for cost reasons for example. Or, a customer could purchase a fully populated system of FIG. 10 or FIG. 11, and some of the detachable detector columns can be removed at a later time. This creates flexibility and upgradability for users and owners of the system. If a particular imaging system user simply focuses on brain imaging in their imaging operations, they may never need the extra detector columns, with related cost and maintenance, of a fully populated system of FIG. 10 or FIG. 11.

Figure 13:
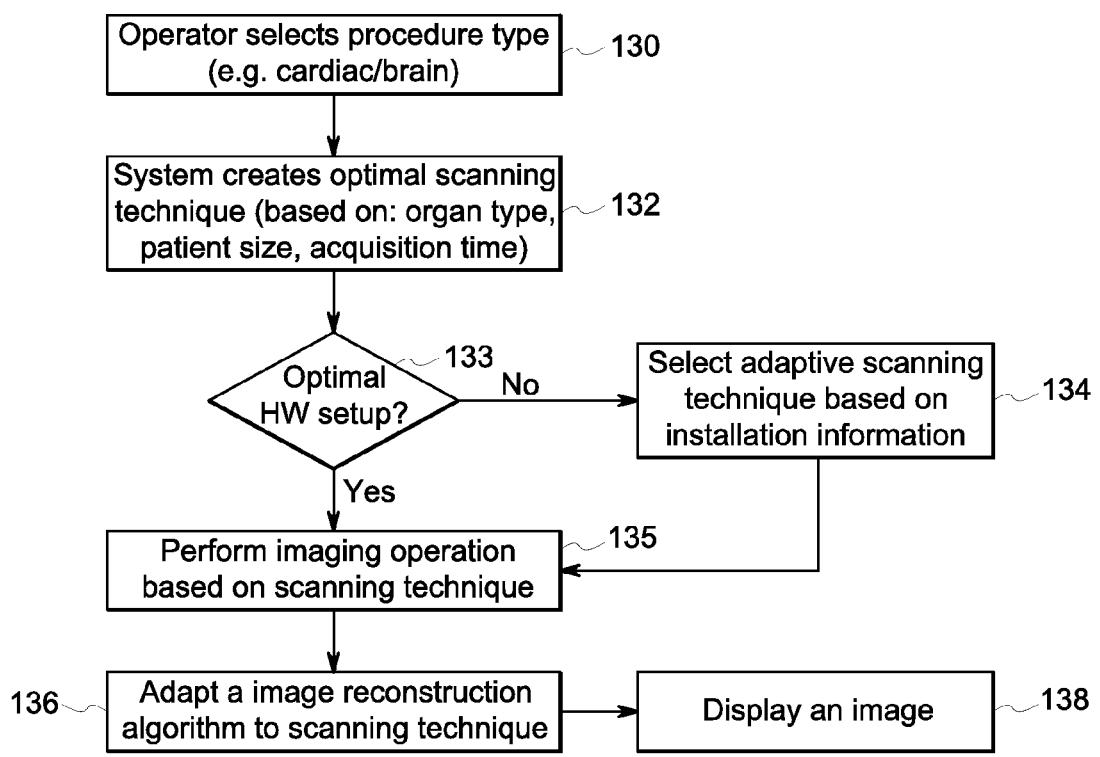
FIG. 13 is a flowchart of a method for controlling detector columns in a partially populated configuration, in accordance with an embodiment.

FIG. 13 shows a flowchart of the operation of the system in an embodiment. In step 130, the system operator gives a user input 39 indicating the procedure type, such as a brain scan, breast scan, cardiac scan, or other object scan.

In step 132, the system creates an optimal scanning technique of how the detector columns 22, detector heads 50, and detector elements 54 should be arranged. This optimal scanning technique can be based on organ type, patient size, desired acquisition time, for example. These can be user input values for each, or system detected values. For example, the patient size could be automatically determined by a quick scan of the environment.

In step 133, the system determines if the hardware installed in the system can perform the optimal scanning technique. This can also be thought of as a determination if the optimal hardware setup is in place for the current situation based on installation information. If the system has all of the hardware installed for an optimal result (meaning the installation information matches the optimal scanning arrangement), the system proceeds to step 135. Otherwise, it proceeds to step 134.

If the system reaches step 134, the system has used the installation information to determine that the optimal scanning technique cannot be performed. This could be, for example, that one detector column is missing so the optimal arrangement cannot be accomplished and the scan time will necessarily be longer. In step 134, the system, using the installation information and/or other factors related to the scan type or scan object, creates a new adaptive scanning technique to meet the situation or retrieves a previously saved adaptive scanning technique from memory that can apply to the current situation. The adaptive scanning technique can add time to the scan, but can be lower cost because the operator or customer does have to pay for a fully populated or fully featured system. Optionally, the adaptive scanning technique may comprise gantry motion or rotation or both in order to bring an operating detector to a location where a missing or inoperative detector should have been.

In step 135, the system performs an imaging operation on the subject. The imaging operation is completed by controlling the hardware elements of the system in a manner fitting the selected scanning technique (either optimal or adaptive). This controlling can include, but is not limited to, extending or retracting detector columns 22, rotating detector heads 50 to different scan angles, or moving detector columns 22 around the gantry orbitally to a new radial angle to the subject (such as the orbital movement of detector columns between FIG. 7A and FIG. 7B).

In step 136, the system adapts a reconstruction algorithm based on an image acquisition scenario and reconstructs the imaging information picked up on the detector elements 54 using imagine reconstruction module 34. This may include updating a system matrix as discussed in conjunction with FIG. 8. The image reconstruction process or algorithm can be adapted to be more compatible with the selected scanning technique. This creates the highest quality image possible given the hardware constraints of the system.

In step 138, the system displays an image output to a user, operator, patient, or other party. This can be on display 40 or at some remote location after the image output has been transmitted over network 42.

Figure 14:
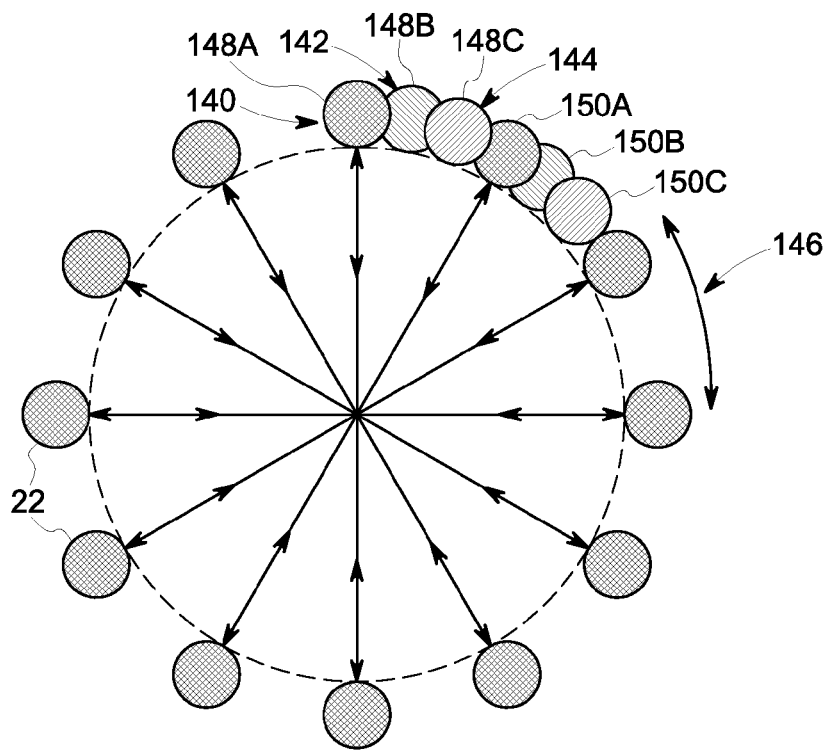
FIG. 14 is a radial construction view of a gantry design with step-enabled detector columns, in accordance with an embodiment.

FIG. 14 shows the ability of the gantry to rotate the detector columns in an orbital manner. Detector columns 22 are placed at even angles from each other in this fully populated example. The gantry rotation range 146 is a full three-hundred sixty degree rotation in some embodiments, as low as zero degrees in other embodiments, and may be anywhere in between. Again, this is an upgradeable feature and related to installation information. The gantry can be initially installed with hardware only supporting thirty degree rotation, for example. The customer could then purchase an upgrade with a few additional motors or hardware components to be installed to give the gantry one-hundred eighty or three-hundred sixty degree rotation ability. FIG. 14 shows a system with a thirty degree gantry rotation range 146. This allows a twelve detector column system to give coverage every ten degrees. FIG. 14 shows detector column 148A at an initial position 140, step one of rotation. Detector columns 148B and 148C are the same physical detector column as 148A, just in new orbital positions 142 and 144, respectively. FIG. 14 further shows detector column 150A rotated to different orbital positions 150B and 150C. Thus, the system can rotate orbitally to move all detector columns to a new radial angle from a subject, or just move specific detector columns to new locations without rotating all of the detector columns in the system. FIG. 14 shows the latter arrangement, when only detector columns 148A and 150A are rotated an all other detector columns 22 remain at the same radial angle with respect to a subject.

Figure 15:
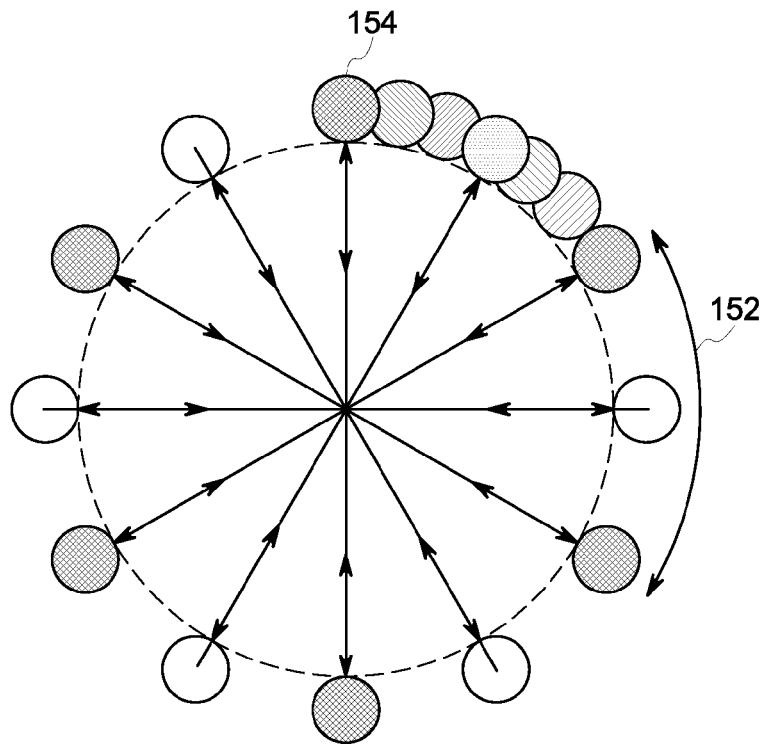
FIG. 15 is a radial construction view of a gantry design with partially populated step-enabled detector columns, in accordance with an embodiment.

FIG. 15 shows the ability of a partially populated gantry to rotate the detector columns, such as detector column 154, in an orbital manner. In this example, the column detectors only partially populate the gantry locations. Six gantry locations, at sixty degree intervals have detector columns installed, while alternating six locations are vacant. The gantry rotation range 152 is sixty degrees in this example, and a detector column 152 has six 'steps' or locations of scanning, each set at a ten degree offset.

Figure 16A:
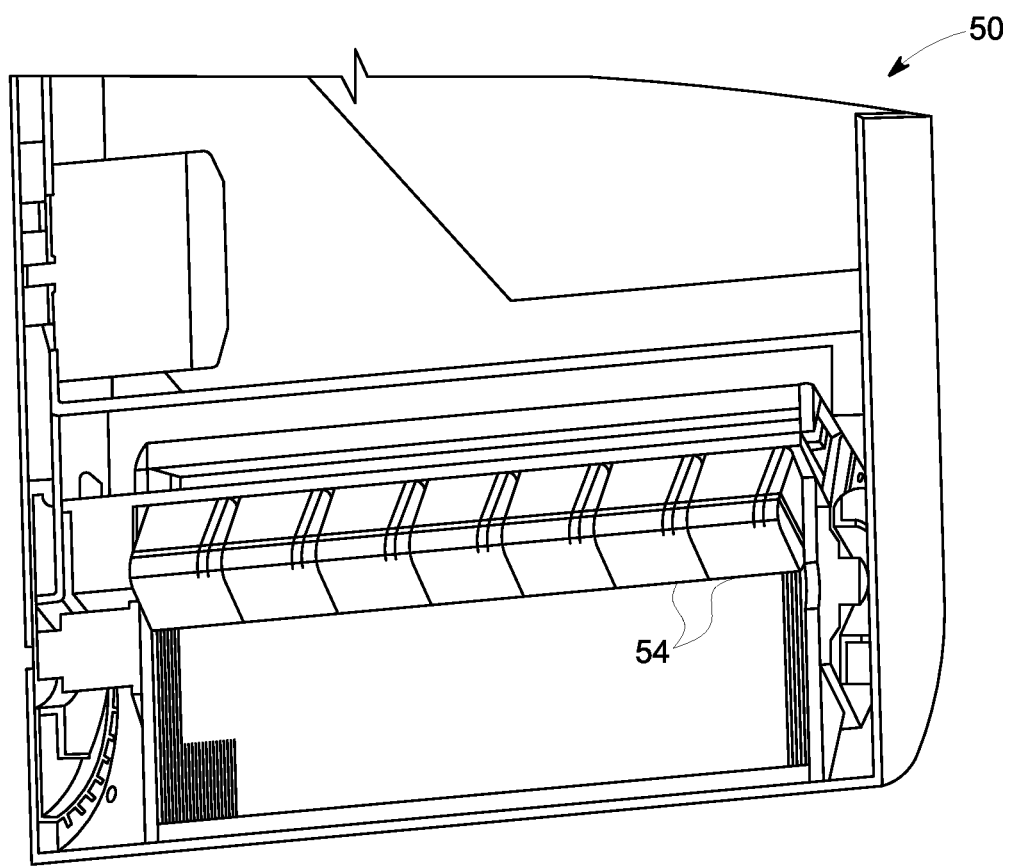
FIG. 16A is a detector column view with fully populated detector elements, in accordance with an embodiment.

FIG. 16A is a detailed view of a fully populated detector head 50. It shows detector elements 54 that include the detector materials to pick up photons or other imaging indicators in an imaging operation. The detector head 50 of FIG. 16A is considered fully populated because all seven of the locations where detector elements can be installed have installed detector elements 54. Whether a detector element 54 is installed or vacant can be one type of installation information. Also, the type of materials embedded in each detector element 54 can be one type of installation information. The head may have any number of detector element locations; seven is just the example of this particular embodiment.

Figure 16B:
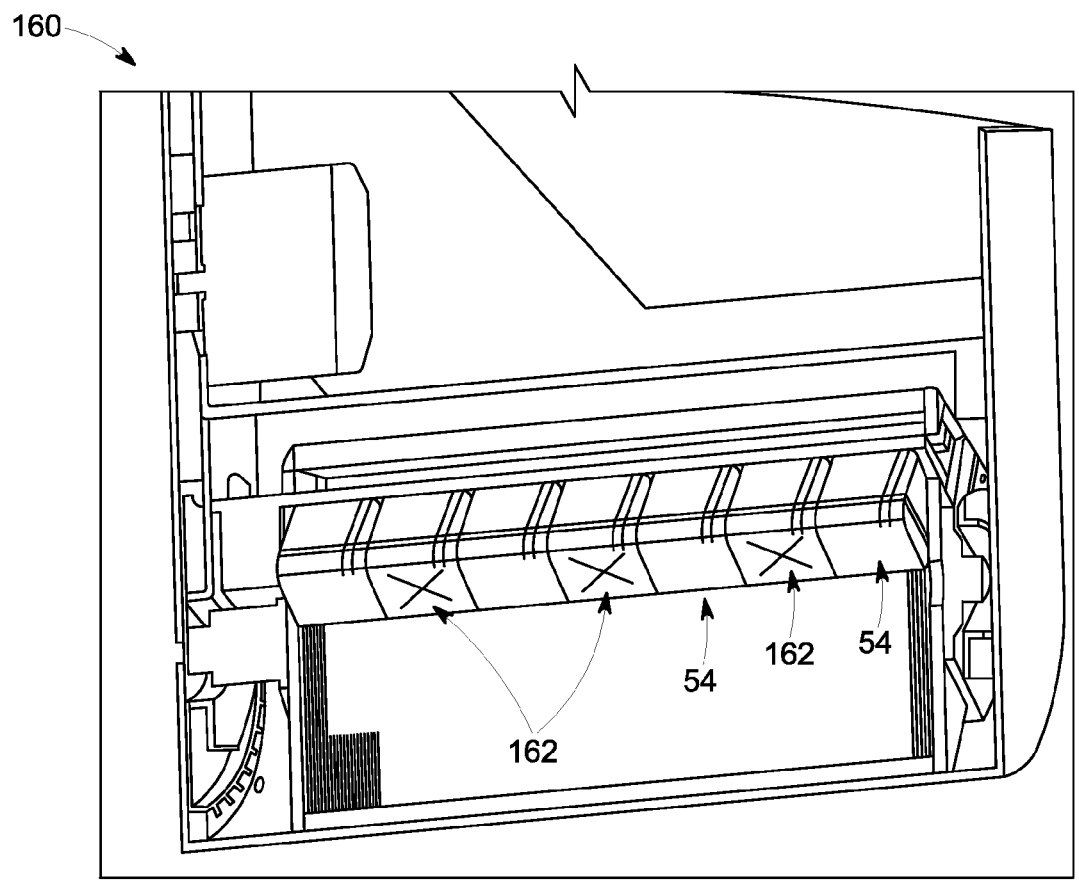
FIG. 16B is a detector column view with partially populated detector elements, in accordance with an embodiment.

FIG. 16B is a detailed view of a partially populated detector head 160. The detector elements 54 are installed in a staggered fashion, with vacant detector element locations 162. This installment configuration provides for a lower cost detector column 22, because much of the cost of a detector column comes from the detector element 54. The collimator may be sized to the number of populated detector elements. In this case, even locations are vacant, and odd locations are populated.

Figure 16C:
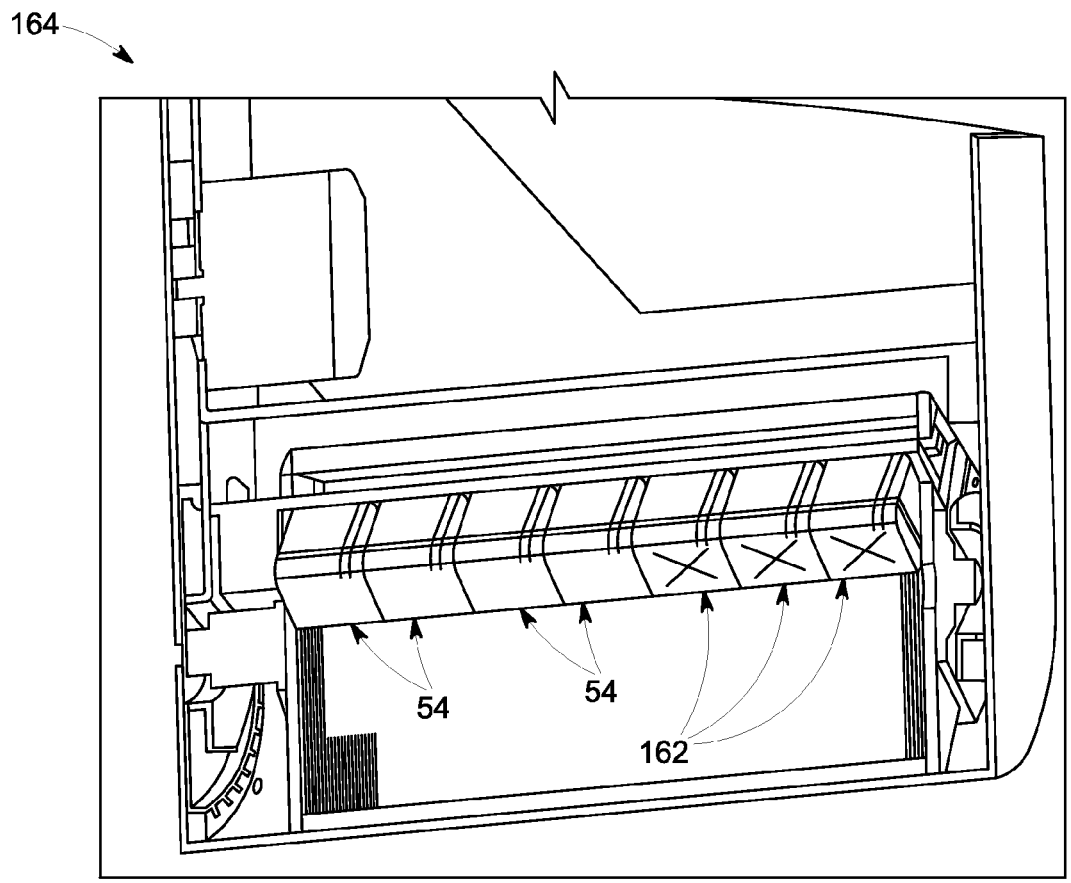
FIG. 16C is a detector column view with partially populated detector elements, in accordance with an embodiment.

FIG. 16C is a detailed view of a partially populated detector head 164. The detector elements 54 are all installed towards one side of the detector head 164. Vacant detector element locations 162 are towards the other side of the detector head 164. This installation configuration can be good for narrow field of view imaging operations. The narrow field of view installation configuration can be good for small organ scanning, such as having five detector elements 54 installed for brain scans (20 cm coverage), four detector elements 54 installed for heart scans (16 cm coverage), or two detector elements 54 installed for thyroid scans (8 cm coverage). As an example, if a system including only two detector elements 54 per detector column 22 was trying to complete a brain scan, the time to do the brain scan could be much longer or the image result could be much worse. Step 86 of FIG. 8 could determine this and notify the user at step 88. The user could then swap out the current detector columns with others that have five detector elements per detector column. The system would then dynamically update the installation information in step 80. Thus, the system is reconfigurable and customizable to fit user needs and imaging situations. A medical facility, for example, in which the majority of scans are of limited axial extend, such as brain, thyroid, heart, and the like may choose the appropriate population for their system to reduce cost. Axial FOV larger than the width of the populated section of the heads, for example, whole body scanning, may be achieved with axial motion of the patient table.

Figure 17A:
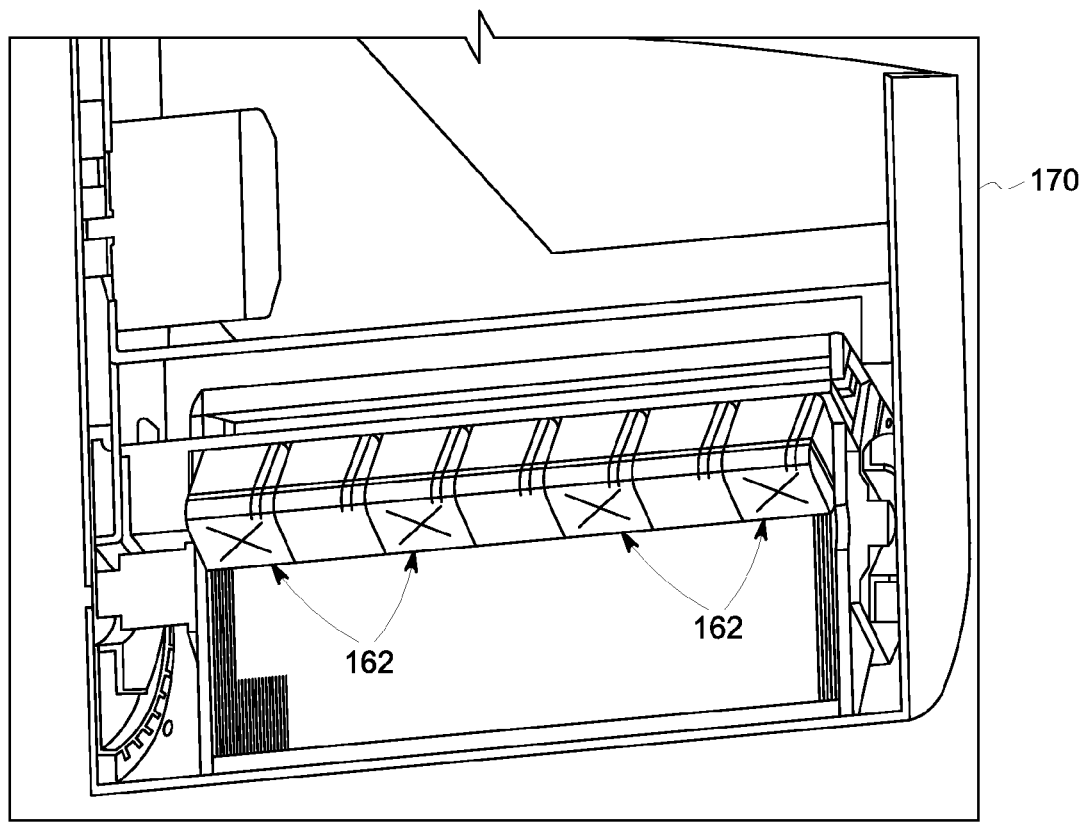
FIG. 17A is a detector column view with only even detector elements populated, in accordance with an embodiment.
Figure 17B:
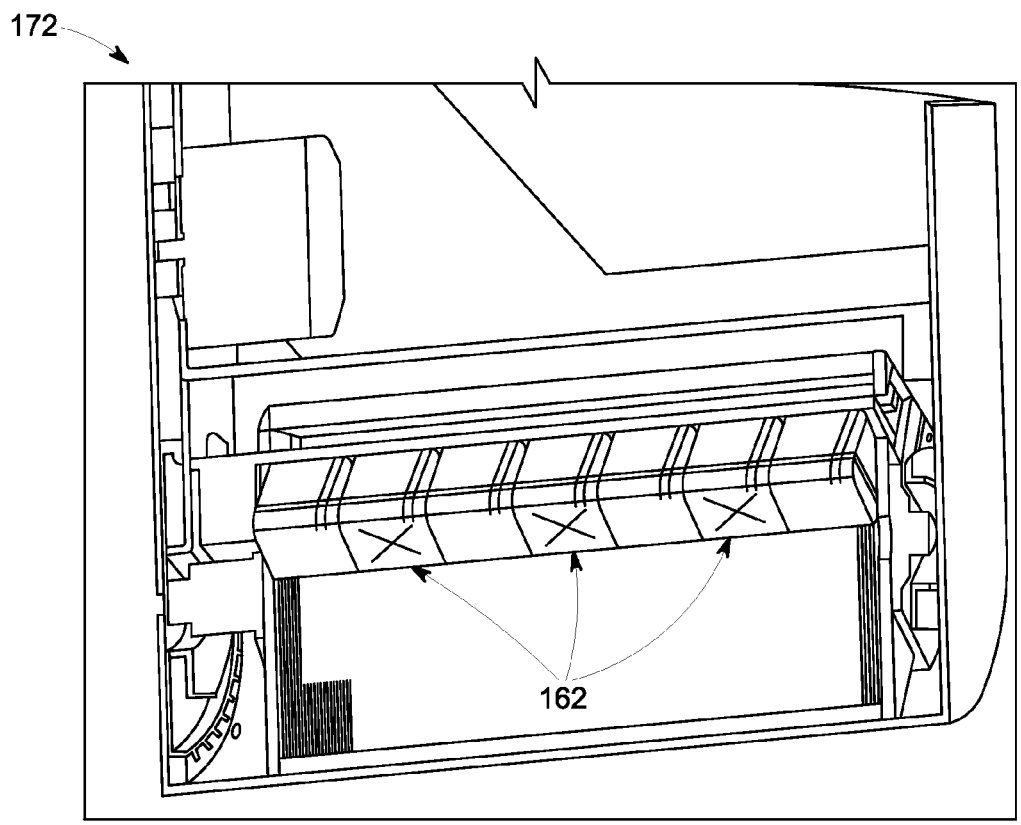
FIG. 17B is a detector column view with only odd detector elements populated, in accordance with an embodiment.

FIG. 17A and FIG. 17B show detailed views of partially populated detector heads. In a system, such as FIG. 20, where a gantry has fully populated detector columns 22, the odd numbered detector columns could have odd populated detector elements, such as in detector head 170. The even numbered detector columns could have even populated detector elements, such as detector head 172. Thus, the installation information can vary from one detector column to the next detector column.

Optionally, the populated detector elements in the detector columns are arranged in an alternating fashion such that a combination of detector elements in two adjacent detector columns creates a full set. This allows for acquiring a full data set by positioning odd columns in the position where an even column was before, and combining the data acquired from the two columns from at the same position. It should be noted that positions may not be identical, but only proximate to enable successful reconstruction. Optionally, adjacent columns may have at least one common populated element or a common missing element and yet enable successful reconstruction. Generally, "over sampling" as created by common populated element is easily compensated in the reconstruction and reduces the noise in the parts of the scanned body which was over sampled. Under sampling as created by common unpopulated element may also be compensated in the reconstruction, but it may increase the noise in the parts of the scanned body which was under sampled. However, not all parts of the body need to be scanned at the same accuracy, and thus under sampling may be tolerated if aimed at less critical organs.

Figure 18:
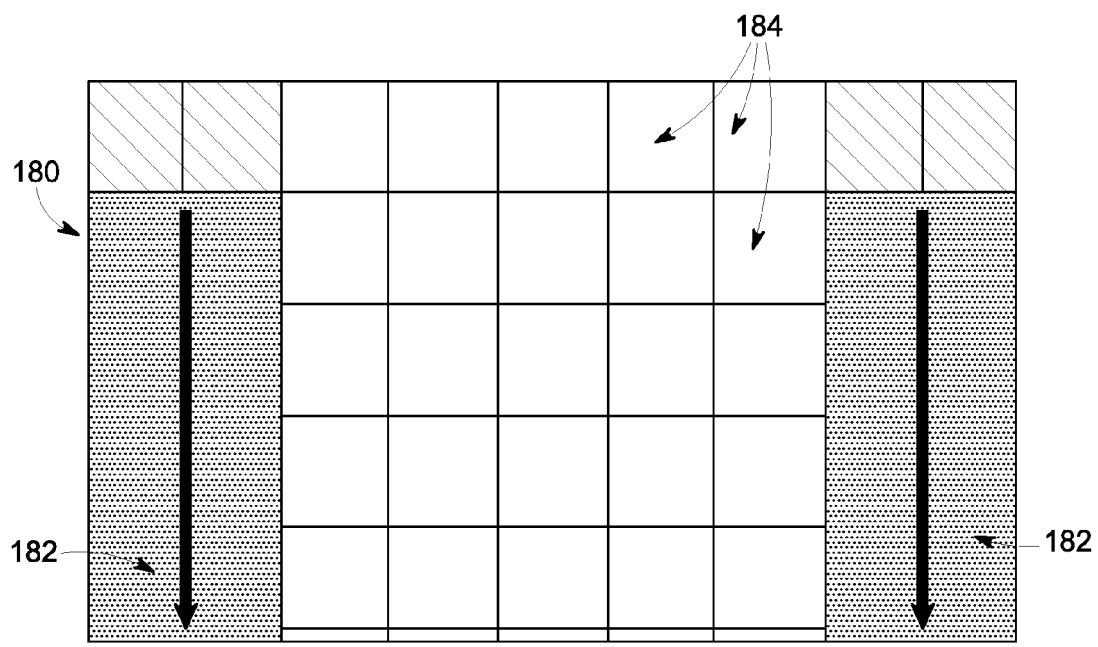
FIG. 18 is a detector element view where the outside detector elements are movable or slide-type, in accordance with an embodiment.

FIG. 18 shows a detailed view of a detector head design of another embodiment. The detector elements of detector head 180 are arranged in a grid. When targeting a specific organ or subject, the direct detector elements are most important for image quality, and the detector elements further to the side are only necessary for peripheral information. Thus, to save cost, detector heads can be configured as shown. The middle region with fixed detector elements 184 give five times better sensitivity than the detector elements 182. This is because sliding detector elements 184 move behind the collimator during the imaging operation to collect data at various points. This movement can be controlled by a motor such as the sweep motor 52 or additional motor installed. The organ or subject, such as a heart, could be centered in the middle of the detector head in an optimal scanning scenario. An effective field of view for such a system could be 36 by 20 centimeters. A quality field of view for such a system could be 20 by 20 centimeters. The installation information for this embodiment can include the number, location, and movement ability of each detector element. The detector head 180 is very useful in system installation configurations where the number of total detector columns is low, because each detector column would be able to handle more detection information. In this embodiment, the collimator could be attached to the detector head itself or individual detector elements. Thus, the movable detector elements 182 could have a collimator attached thereto so that a collimator would not have to be manufactured for the whole space, saving cost.

Figure 19:
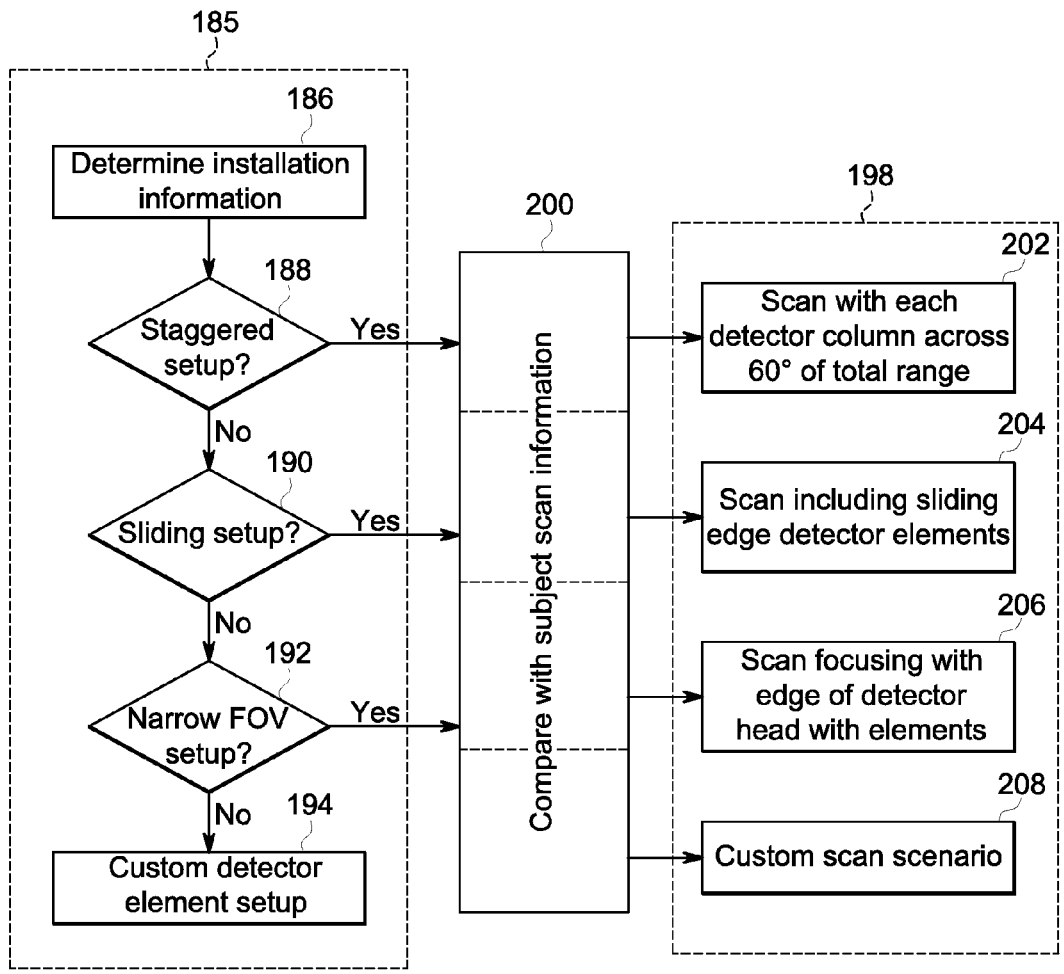
FIG. 19 is a flowchart of a method for controlling detector columns where detector elements are partially populated, in accordance with an embodiment.

FIG. 19 is a flowchart of one embodiment in which different detector element configurations are applicable to the installation information. Dotted box 185 indicates that the steps 186-194 are examples of the types of determinations that could be made in step 80 of FIG. 8. Step 200 is an example of type of determination that could be made in step 82 of FIG. 8. And dotted box 198 indicates that the steps 202-208 are examples of the types of determinations that could be made in step 84 of FIG. 8.

In step 186, the system collects data from various parts of the overall system (such as shown in steps 71-75 of FIG. 8). Based on that data, the system determines whether the system has a staggered setup, in step 188, a sliding setup, in step 190, a narrow FOV setup, in step 192, or a custom detector element setup, in step 194. A staggered setup could be one such as demonstrated in FIGS. 17A and 17B. A sliding setup could be one such as demonstrated in FIG. 18. A narrow FOV setup could be one such as demonstrated in FIG. 16C.

In step 200, the system compares the determined detector element setup from the steps of dotted box 185 with subject scan information. This information is based on the subject of the scan (i.e. heart, thyroid, brain, breast, etc.) as well as the type of scan being performed.

In the steps of dotted box 198, an imaging operation is performed based on the installation information compared with the subject scan information. If there is a good fit between the installation information, the corresponding scan to the detector element is selected. This is indicated by the horizontal lines. Step 202 to scan with each detector column across sixty degrees of the total range (such as in FIGS. 20A-20C) is generally performed when the staggered setup is determined in step 188 and that matches well with the subject scan information. Step 204 to scan including sliding edge detector elements is generally performed when the sliding setup is determined in step 190 and that matches well with the subject scan information. Step 206 to scan focusing with edge of a detector head with installed elements is generally performed when the narrow FOV setup is determined in step 192 and that matches well with the subject scan information. Step 208 to scan using a custom scan scenario is generally performed when the installation setups do not match with the subject scan information or are not in any predefined arrangement.

Figure 20A:
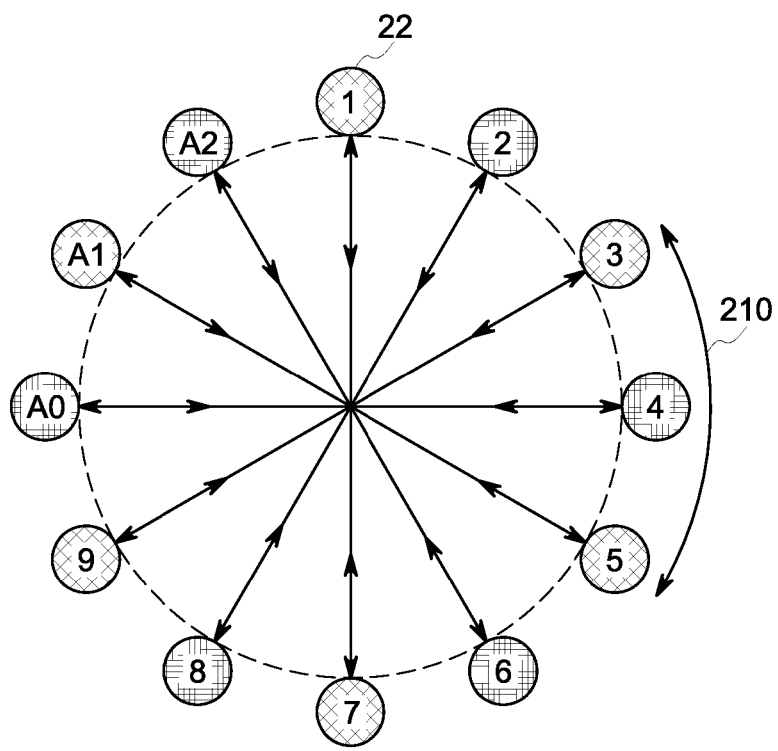
FIG. 20A is a radial construction view of a starting-position gantry system where detector elements are partially populated, in accordance with an embodiment.
Figure 20B:
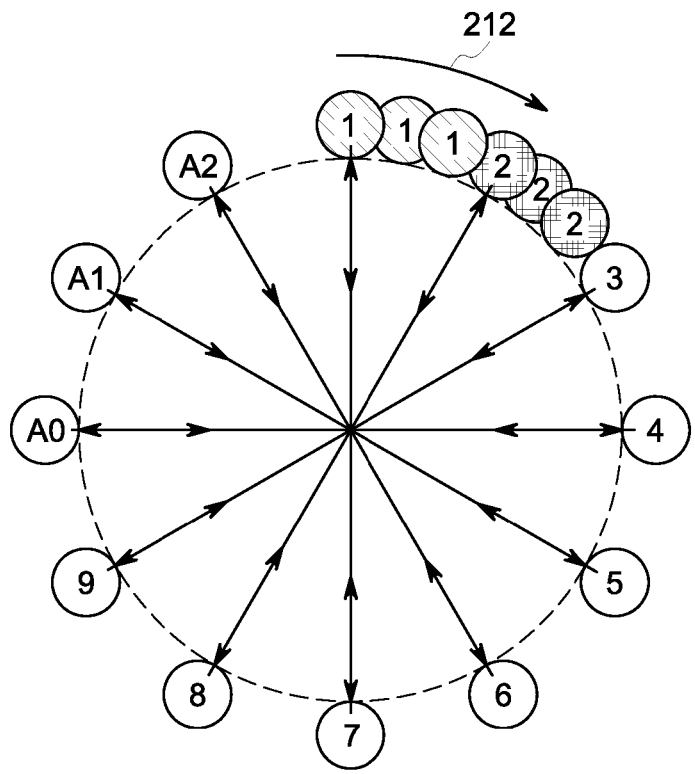
FIG. 20B is a radial construction view of moving detector columns in a gantry system where detector elements are partially populated, in accordance with an embodiment.
Figure 20C:
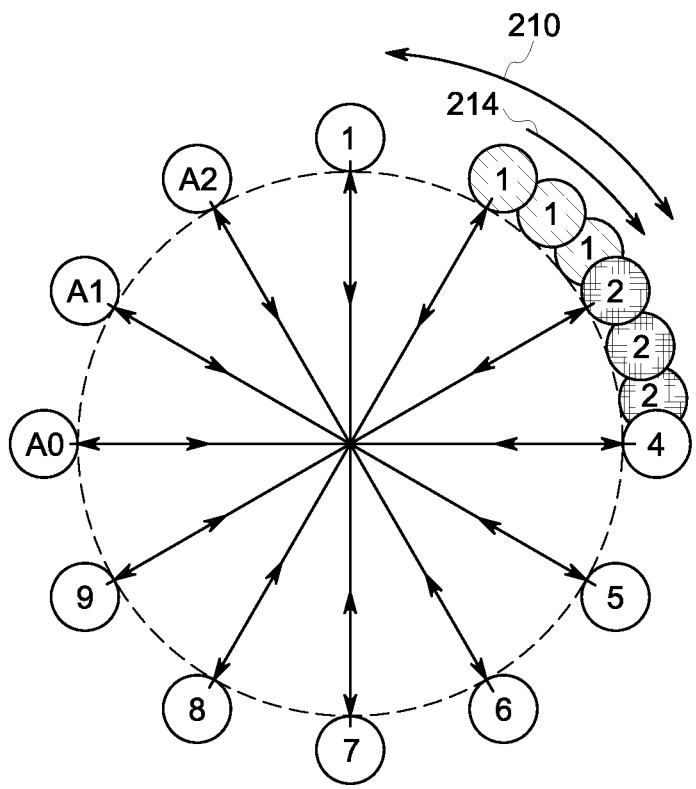
FIG. 20C is a radial construction view of moving detector columns in a gantry system where detector elements are partially populated, in accordance with an embodiment.

FIGS. 20A-20C show the details of an imaging operation of step 202 where each detector column scans across sixty degrees across the total range. This could be best executed for a system of FIGS. 17A and 17B as discussed in detail above. Odd detector columns have odd detector elements installed and even detector columns have even detector elements installed. Therefore, to get a full scan of the subject, the system would have to orbitally rotate each detector column sixty degrees during the total imaging operation.

FIG. 20A shows a system with fully populated detector columns 22 with a gantry orbital rotation range 210 of sixty degrees. The detector arms can be extended radially in the system. While the detector columns are fully populated, the detector elements in each detector column are not, as discussed above.

FIG. 20B shows a staggered imaging operation during the first three movement locations, covering a gantry orbital rotation range 212 of thirty degrees.

FIG. 20C shows a staggered imaging operation during the final three movement locations, covering an additional gantry orbital rotation range 214 of thirty degrees. Thus, each angle of a scanning operation is covered by an even and an odd detector element. The imaging operation may take longer than a system with fully populated detector elements, but the system can be cheaper due to having only half of the total detector elements in the system.

Figure 21:
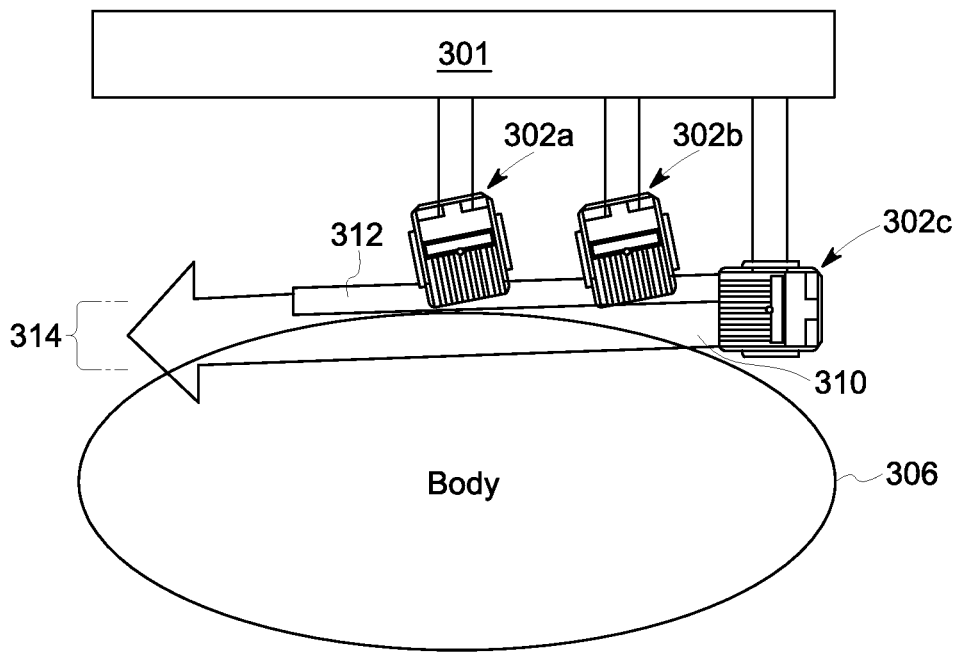
FIG. 21 is a front view of an imaging system showing an obstruction, in accordance with an embodiment.

FIG. 21 is a front view of an imaging system showing an obstruction, in accordance with an embodiment. Gantry 301 supports detector columns, with three shown in FIG. 21, in an embodiment. Detector heads 302a, 302b, and 302c are part of their respective detector columns.

FIG. 21 shows the sweep motion of a detector head, as described above in conjunction with FIG. 3. In the image scanning of patient body 306, detector head 302c pivots, or sweeps, to the position shown in FIG. 21. The field of view 314 includes both unobstructed view 310 and obstructed view 312. Unobstructed view 310 includes no objects between the area to be scanned and detector head 302c. Obstructed view 312 includes at least one object between the area to be scanned and detector head 302c. In this position, the system may still want to operate an image scan to collect image data in unobstructed view 310, but may not need any of the image data being gathered related to obstructed view 312.

In various embodiments, each of the detector columns includes a position sensing device, such as one or more positions sensors or encoders that are used to determine the orientation and/or angle of rotation of each of the detector columns. It should be noted that the position sensors may also be used to determine the location or position of the detector column along other axes of movement. For example, if one or more of the detector columns is capable of linear movement or movement along or about other axes, the position sensors are configured to detect the location or position of the detector column as a result of any such movement. In various embodiments, one or more position sensors may be provided in connection with each of the detector columns. Additionally, the position sensors may determine, for example, the position or orientation of the detector column to which the position sensor is attached and optionally the relative position or orientation of another detector column, such as an adjacent detector column. Thus, the position sensor may be configured to detect the position of the detector column along multiple axes of movement and/or rotation. For example, the position sensors may be configured to determine the position and/or orientation of the detector columns within a three-dimensional space, such as the X, Y, Z location of the detector columns within a patient support structure. For example, one or more of a proximity sensor (e.g., optical sensor) and/or rotary encoder (e.g., angular sensor) may be used. Accordingly, in various embodiments the position sensors may be linear, angular and/or multi-axis position sensors. Additionally, the position sensors may be absolute position sensors and/or relative position sensors (e.g., displacement sensors). In some embodiments, a Global Positioning System (GPS) arrangement may be provided. It should be noted that in some embodiments, any suitable position sensor as known in the art also may be used. Additional ways of detecting the position and orientation of the system may be used. For example, anytime one of the sweep motor, radial motion motor, or arm pivot motors is adjusted, it may record the adjustment to keep a record of the system geometries.

In operation, based on the determined position and/or orientation (e.g., rotated angle) of the detector columns, and in some embodiments, using the known size of the detector columns or the known size of the field of view of the detector heads, a determination may be made as to whether the field of view of one of the detector columns is being obstructed or will be obstructed by another one of the detector columns, as well as whether a collision may occur.

Figure 22:
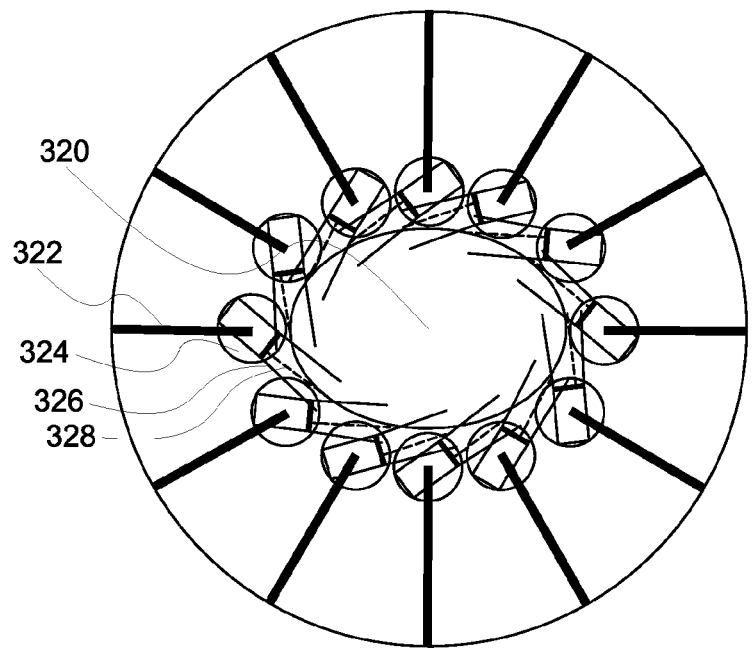
FIG. 22 is a front view of an imaging system showing multiple obstructions, in accordance with an embodiment.

FIG. 22 is a front view of an imaging system showing multiple obstructions, in accordance with an embodiment. A fully populated system is shown in FIG. 22. A subject 320 of an imaging operation is placed in the bore of the gantry. Detector columns 322 include detector heads 324. Detector heads 324 have all been extended to a close proximity to subject 320. Detector heads 324 have all been swept, or pivoted, clockwise to where they are receiving image data from the exterior edges of subject 320. In this position, each detector head 324 has its field of view (FOV) 326 include both obstructed and unobstructed areas. As an example, this is shown by dividing line 328 in FIG. 22. Thus, allowing the obstruction (by updating the system matrix as discussed herein) and continuing to perform an image scan helps the system get high quality images of subject 320.

Figure 23:
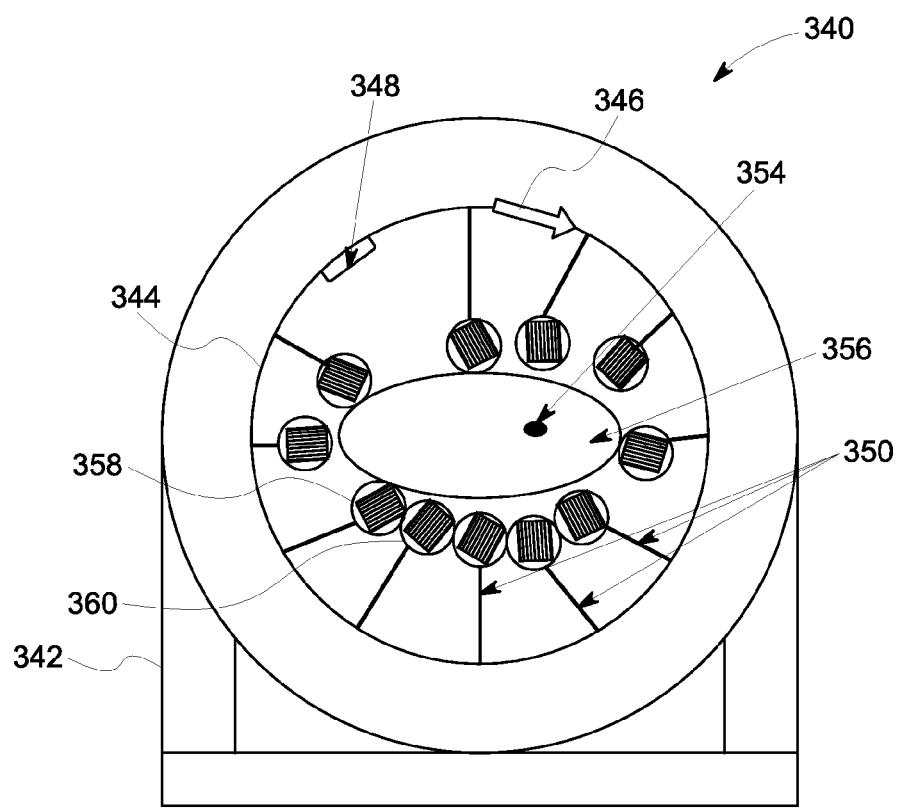
FIG. 23 is a front view of an imaging system during an imaging operation, in accordance with an embodiment.

FIG. 23 is a front view of an imaging system 340 during an imaging operation, in accordance with an embodiment. Stationary gantry 342 includes rotary member 344. In an exemplary operation, rotary member is rotating clockwise, as shown by direction arrow 346. A patient 356 is resting on a table (not shown) and includes region of interest (ROI) 354. All of the receiver locations, except for empty receiver location 348, include detector columns 350. Some detector columns are fully extended along the detector arm and some are only partially extended towards patient 356. All detector heads in detector columns 350 have been swept to be targeted at ROI 354. Some detectors have a fully clear FOV, such as detector column 360. Some detectors have a partially obstructed FOV, such as detector column 358. In operation, the system may rotate rotary member 344 orbitally around the bore, extend or retract detector columns 350, pivot detector columns (adjusting the angle the detector column arm extends from the rotary member), and/or sweep detector heads. In each instance of a change, the system may update the system matrix.

Figure 24:
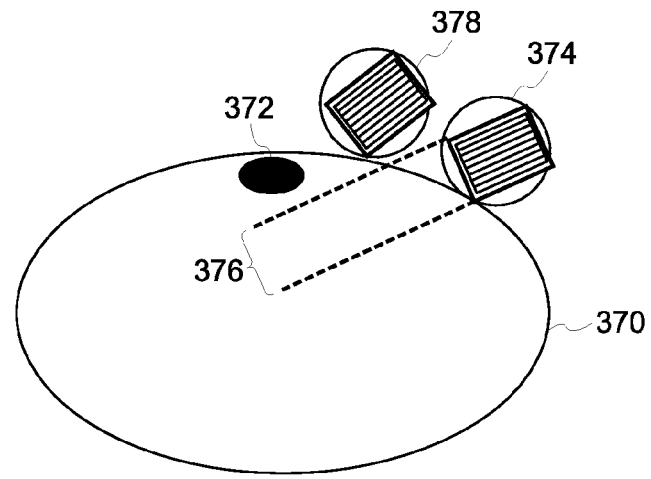
FIG. 24 is a detailed view of an imaging detector rotation with no obstruction, in accordance with an embodiment.
Figure 25:
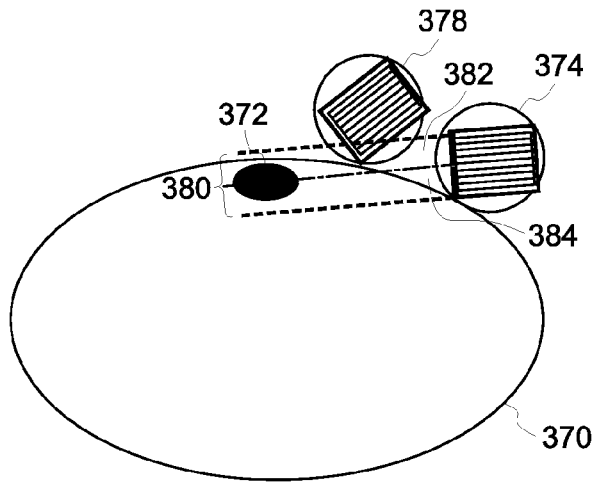
FIG. 25 is a detailed view of an imaging detector rotation with an obstruction, in accordance with an embodiment.
Figure 26:
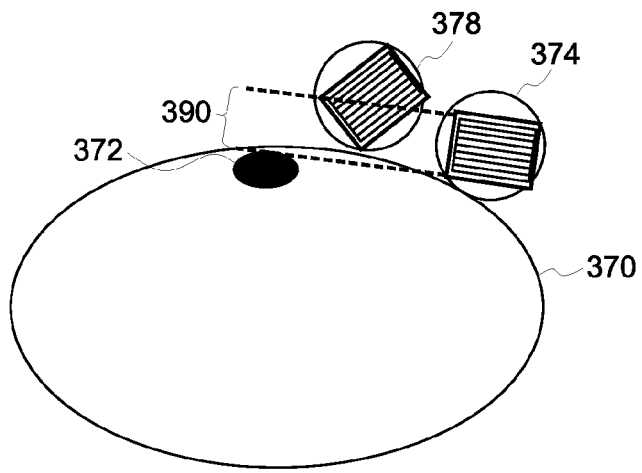
FIG. 26 is a detailed view of a completed imaging detector rotation in an obstruction scenario, in accordance with an embodiment.
Figure 27:
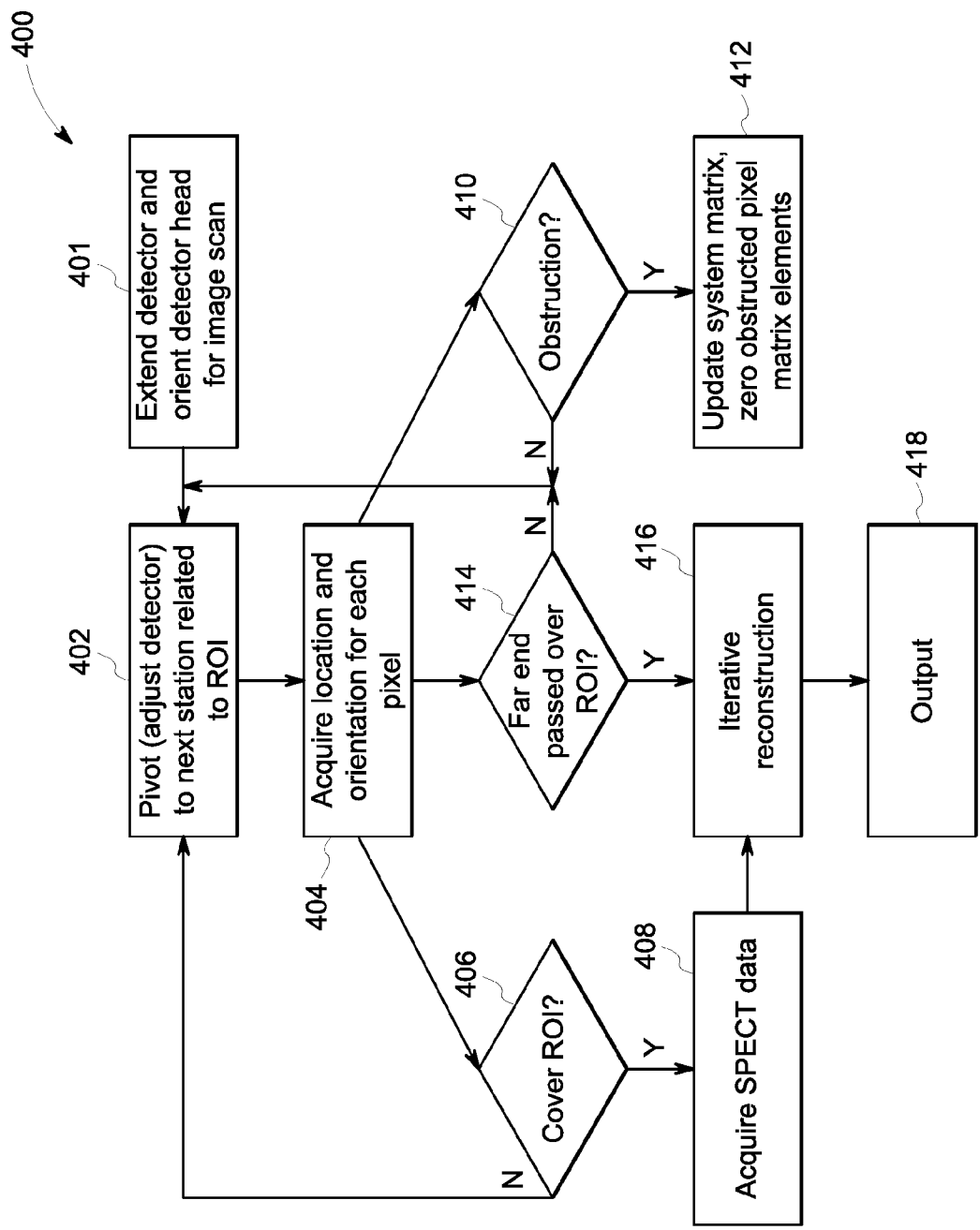
FIG. 27 is a method for increasing image quality in an imaging system with obstructions, in accordance with an embodiment.

FIGS. 24-27 will be discussed in conjunction with one another describing the operation of an imaging system, in accordance with an embodiment. FIG. 24 is a detailed view of an imaging detector rotation with no obstruction, in accordance with an embodiment. FIG. 25 is a detailed view of an imaging detector rotation with an obstruction, in accordance with an embodiment. FIG. 26 is a detailed view of a completed imaging detector rotation in an obstruction scenario, in accordance with an embodiment. FIG. 27 is a method 400 for increasing image quality in an imaging system with obstructions, in accordance with an embodiment.

The system depicted is only a limited view of the full system described with reference to earlier figures. A subject 370 is being imaged from internal emissions, primarily emanating from ROI 372. Detector head 378 is directed towards ROI 372 for the imaging operation. Moving detector head 374 has a FOV 376. Initially, in FIG. 24, FOV 376 does not cover ROI 372. As moving detector head 374 sweeps clockwise towards ROI 372, ROI 372 enters the obstructed FOV 380. FIG. 25 shows how moving detector head 374 now has ROI 372 in its obstructed FOV 380, but also has some of its view obstructed by detector head 378. The system can be aware of such an obstruction through presence sensors, installation information, and/or system matrix information. In this case, valid pixels 384 can be processed in image reconstruction, while invalid pixels 382 can be ignored, as discussed with reference to step 412. Moving detector head 374 continues to sweep, or pivot, clockwise to get additional image data related to ROI 372. FIG. 26 shows the point where a current FOV 390 no longer contains ROI 372. This situation where a detector head FOV has completed its pass over an ROI is also referred to as its FOV "far end" passing over ROI. Thus, at this point, the system can perform iterative reconstruction and output the final image. Thus, the system may be aware of an obstruction, but still intentionally positions a detector head where it will be obstructed in order to obtain certain image data from a subject.

It should be noted that the FOV of a particular detector head may not be the full width of its collimator, as shown in FIG. 24. It may be a partial amount if the detector head is only partially populated with detector elements, as shown in FIGS. 16B and 16C. Thus, the FOV would be a reduced amount. The system can determine the proper FOV for each detector head in the system using installation information.

FIG. 27 shows imaging method 400 for operating in such obstruction conditions. It should be noted that the order of the steps of FIG. 27 show only one particular embodiment. The order and progression of the method may be altered depending on system needs.

In step 401, prior to acquiring an image of a subject or a portion of the subject, the imaging detectors columns, detector heads, gantry, patient table and/or collimators may be adjusted as discussed in more detail herein, such as to first or initial imaging positions, as well as subsequent imaging positions. The system, as needed, extends the detector heads along their respective detector arms, rotates the rotary member to adjust the location of the detector columns around the circumference of the bore, and/or sweep the detector heads as needed. This may include extending the detector head and orient the detector head for an image scan. This may be as discussed with relation to FIG. 8, for example. Positioning may be accomplished manually by the operator and/or automatically, which may include using other images acquired before the current acquisition, such as by another imaging modality such as CT, MRI, X-Ray, PET or ultrasound. Additionally, the detector heads may be configured to acquire non-NM data, such as x-ray CT data or PET data.

In step 402, the system pivots, or sweeps, a detector head to the next station related to an ROI, such as ROI 372. This is shown, in one embodiment, through detector head 374. For example, the initial positioning for detector head 374 is shown in FIG. 24, then the system can adjust the detector head angle successively each time step 402 is performed until the detector head is positioned as shown in FIG. 25, and then finally FIG. 26. Additional system configuration adjustments may be made as discussed throughout.

In step 404, the system acquires the location and orientation information for each pixel. Each pixel may correspond to a detector element or a smaller sub-portion within a detector element. This step may also determine what detector elements are installed in a given detector head. Thus, obstructions may not exist for some detectors compared to others based on the detector element configurations in each respective detector head. Each time the system acquires such location and orientation information, the installation information and/or the system matrix may be updated as discussed throughout. After step 404, the system proceeds to steps 406, 414, and 410, which may be performed in parallel or sequentially.

In step 406, the system makes a determination whether the field of view of the particular detector head covers any part of the ROI. Examples are FOV 376, obstructed FOV 380, and FOV 390. The system may include additional areas around the ROI to be included in an "expanded ROI" area. If the answer is NO, such as in FIG. 24, the system proceeds to step 402. If the answer is YES, such as in FIG. 25, the system proceeds to step 408. It should be noted that there may be times when a detector head is obstructed to the extent that at a certain location, the full sweep of the detector head may not cover any of the ROI. In this circumstance, no data from that detector is needed in image reconstruction.

In step 408, the system acquires SPECT data from the detector head. The detector head has some of its FOV in the ROI. This SPECT data will be used by the system to reconstruct an image in step 416. In an alternate embodiment, the system may acquire all SPECT data and then filter later. But in this embodiment, the system tries to pre-filter by only collecting SPECT data if the ROI is included in the data. The pre-filter step of 406 may speed up system image acquisition and image reconstruction.

In step 410, the system makes a determination of whether there is an obstruction in the FOV of the detector head, such as in FIG. 25. The obstruction determination may be a combination of determining the location of the detector heads, which may change during the scan (rotation angles, radial positions, sweep angles), and the fixed dimensions of the heads (column diameter, center of rotation position). With this information, the system may perform geometric calculation to determine whether there is an obstruction in each view, and which pixels are obstructed. The obstruction determination may be performed through presence sensors, installation information, detector controller 30, and/or system matrix information. If the decision is YES, there is an obstruction, the system proceeds to step 412. Otherwise, the decision is NO, and the system proceeds to step 402.

In step 412, the system updates the system matrix, which may include zeroing out the matrix elements that include an obstructed pixel. Thus, the system matrix used in image reconstruction can be dynamically changed to take into account the times and positions of when obstructions occur. By zeroing out the matrix elements related to obstructions, any acquired image data by the detector head in the obstruction is treated as if it did not exist when reconstruction occurs. This is because the system matrix is applied to the raw acquired SPECT data during image reconstruction. This step helps to improve image reconstruction and reduce artifacts in the final output image.

In step 414, the system makes a determination of whether the FOV "far end", as discussed above, has fully passed over the ROI. Put another way, the system determines whether the detector head has completed its full sweep over the ROI. A full sweep could include passing over ROI multiple times in an embodiment. See FIG. 26 for example. This may include determining whether a ROI is within a field of view of the detector head and stopping the pivoting of the detector head if a detector pixel in the field of view reaches an end of the ROI before reaching an obstruction. The obstruction may be caused by other detectors in the system, according to an embodiment. If the determination is YES, the system proceeds to step 416. If the determination is NO, the system proceeds to step 402 to continue the detector head sweep of the ROI.

In step 416, the system performs iterative reconstruction of the acquired SPECT data utilizing the system matrix. Iterative reconstruction may be performed in parallel to, or, as the method shows, after the full ROI has been scanned by a detector head.

In step 418, the system can output the reconstructed image to a display, printer, computer network, or other device. The output image may comprise two-dimensional (2D) images, a three-dimensional (3D) volume or a 3D volume over time (4D).

FIGS. 24-27 illustrated a particular example for a single detector head movement. The system, as noted throughout, has many forms of movement that may be happening throughout all detector columns over the course of an imaging operation. All such movement may impact the updated system matrix. The same line of view may happen a few times as a single detector column sweeps its detector head. Further, multiple detector column can target the same area, potentially even from the same location and direction if the system has rotated the detector column orbitally to the same position of the previous detector column. Thus, the system can compare the line of view of one pixel from one detector column to the information of a pixel at the same line of view of a different detector column that had moved and oriented to the same line of view (as detectors rotate around the bore and heads pivot). In addition, as different detector columns can be populated with differing scintillation materials and collimators, this may provide enhanced information useful to image reconstruction and medical diagnosis.

As contemplated, the various embodiments provide a lower cost, upgradable, and customizable system for imaging operations. In addition, the system can put detector heads closer to a subject as well as perform sweeps at close proximity with the system and methods herein. Both of these features improve image quality. This is because, among other things, obstructed pixels are aimed outside of the subject, and their obstruction does not constitute loss of data. Leaving the data from the obstructed pixels can create inconsistencies of the data and may cause artifacts. Thus, the system matrix updating improves image quality. This is because the system reduces artifacts in the image that may be caused by some detector heads obstructing the FOV of the neighboring detectors while having detector elements at a closer proximity to the patient and region of interest.

The configurable and controllable system of some embodiments could be controlled by user input. Thus, the user can override the automatic operation of the system and take full specific control of components of the system through a user interface. While the foregoing description focuses on medical imaging, nuclear imaging in specific, these methods and systems can be applied to other systems where multiple cameras are used to retrieve image data of one or more subjects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a flash memory disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system comprising:
a gantry;
a plurality of imaging detector units, each detector unit comprising a detector arm installed in the gantry and a detector head; wherein at least one of the detector heads is movable such that its angle can be altered with respect to its detector arm;
a controller in communication with the plurality of detector units, configured to control the angle of the at least one detector head; and wherein if the controller detects an obstruction in a field of view of a detector head, the controller updates a system matrix to include obstruction information related to the obstruction.

2. The imaging system of claim 1, wherein the controller:
receives image information detected by the detector units;
reconstructs the image information into images using the updated system matrix; and
outputs the images to a display, printer, memory, or computer network.

3. The imaging system of claim 1, wherein the controller performs the steps of:
adjusting the angle of a detector head;
acquiring location and orientation information for the detector head at its new angle;
generating a field of view determination for the detector head based on said location and orientation information;
determining whether a region-of-interest (ROI) of an imaging subject is within the detector field of view;
if the ROI is within the field of view, the controller acquires image information detected by the detector head even if an obstruction is within the field of view; and
if the ROI is outside the field of view, the controller does not acquire image information detected by the detector head.

4. The imaging system of claim 3, wherein:
the controller acquires the location and orientation information from a position sensor installed in the detector unit.

5. The imaging system of claim 1, wherein:
the updating of the system matrix to include obstruction information includes inputting zeros into the matrix elements related to the pixels that are obstructed.

6. The imaging system of claim 1, wherein:
the detector head movement is a pivot movement with respect to its respective detector arm.

7. The imaging system of claim 1, wherein:
each detector head is extendable and retractable with respect to the gantry along its respective detector arm.

8. The imaging system of claim 1, wherein:
each detector head includes a plurality of detector elements that detect SPECT emissions.

9. The imaging system of claim 1, wherein:
the system matrix is a data structure in memory that describes the physics of the imaging system.

10. An imaging method, comprising:
pivoting a detector head of an image detector unit, the image detector unit attached to a gantry;
determining whether an obstruction is in the field of view of the detector head; and
updating a system matrix to include information related to the obstruction.

11. The imaging method of claim 10, further comprising:
acquiring location and orientation information for the detector head at its current angle;
generating a current field of view determination for the detector head based on said location and orientation information;
determining whether a region-of-interest (ROI) of an imaging subject is within the detector current field of view;
if the ROI is within the current field of view, a controller acquires image information detected by the detector head even if an obstruction is within the field of view; and
if the ROI is outside the current field of view, the controller does not acquire image information detected by the detector head.

12. The imaging method of claim 10, further comprising:
receiving image information detected by the detector unit;
reconstructing the image information into images using the updated system matrix; and
outputting the images to a display, printer, memory, or computer network.

13. The imaging method of claim 12, wherein:
the image information includes SPECT information.

14. The imaging method of claim 10, wherein:
the updating of the system matrix to include information related to the obstruction includes inputting zeros into the matrix elements related to the pixels that are obstructed.

15. The imaging method of claim 10, further comprising:
updating the system matrix based on installation information and subject scan information.

16. The imaging method of claim 10, wherein:
the detector head comprises a plurality of detector elements and a collimator;
the field of view is determined by the coverage of said detector elements and a collimator configuration.

17. The imaging method of claim 10, further comprising:
determining whether a ROI is within a field of view of the detector head;
second pivoting of the detector head in the same direction as the first pivoting if the ROI is within the field of view; and
stopping the pivoting of the detector head if a detector pixel in the field of view reaches an end of the ROI before reaching an obstruction.

18. A non-transitory computer readable storage medium having stored thereon a computer program comprising instructions, which, when executed by a computer, cause the computer to:
issue an instruction to pivot a detector head of an image detector unit, the image detector unit attached to a gantry;
determine whether an obstruction is in the field of view of the detector head; and
update a system matrix to include information related to the obstruction.

19. The computer readable storage medium of claim 18, further causing the computer to:
acquire location and orientation information for the detector head at its current angle;
generate a field of view determination for the detector head based on said location and orientation information;
determine whether a region-of-interest (ROI) of an imaging subject is within the detector field of view;
if the ROI is within the field of view, acquire image information detected by the detector head even if an obstruction is within the field of view; and
if the ROI is outside the field of view, not acquire image information detected by the detector head for the current position of the detector head.

20. The computer readable storage medium of claim 18, further causing the computer to:
receive image information detected by the detector units;
reconstruct the image information into images using the updated system matrix; and
output the images to a display, printer, memory, or computer network.

* * * * *